US006274341B1

(12) United States Patent
Bailey et al.

(10) Patent No.: US 6,274,341 B1
(45) Date of Patent: Aug. 14, 2001

(54) CYTOSTATIC PROCESS INCREASES THE PRODUCTIVITY OF CULTURED CELLS

(76) Inventors: James E. Bailey, Winkelwiese 6, Zürich (CH), CH-8001; Martin Fussenegger, Regulastrasse 54, Zürich (CH), CH-8046; Wolfgang A. Renner, Weinbergstrasse 64, Zürich (CH), CH-8006

( * ) Notice: Subject to any disclaimer, the term of this patent is extended or adjusted under 35 U.S.C. 154(b) by 0 days.

(21) Appl. No.: 08/948,381

(22) Filed: Oct. 9, 1997

(51) Int. Cl.[7] .............................. C12P 21/02; C12N 5/10; C12N 15/85
(52) U.S. Cl. .................. 435/69.2; 435/69.1; 435/69.4; 435/69.5; 435/69.51; 435/69.52; 435/69.6; 435/320.1; 435/455; 435/325; 435/367; 435/358; 435/352; 435/348; 435/357; 435/365; 435/370; 435/372; 435/372.3; 435/371; 435/366; 435/372.2
(58) Field of Search ...................... 435/69.1, 5, 6, 435/69.2, 69.4, 69.5, 69.51, 69.52, 69.6, 320.1, 455, 325, 367, 358, 352, 348, 357, 365, 370, 372, 372.3, 371, 366, 372.2

(56) References Cited

PUBLICATIONS

Di Leonardo et al., 1993, *Cold Spring Harbor Symp. Quant. Biol.* 58:655–667.
El–Deiry et al., 1994, *Cancer Res.* 54:1169–1174.
Greenblatt et al., 1994, *Cancer Res.* 54:4855–4878.
Kastan et al., 1991, *Cancer Res.* 51:6304–6311.
Kromenaker and Srienc, 1991, *Biotechnol. Bioeng.* 38:655–677.
Liu et al., 1995, *Cancer Res.* 55:3117–3122.
Liu et al., 1994, *Cancer Res.* 54:3662–3667.
Marcus et al., 1985, *Ann. Rev. Genet.* 19:389–421.
Robinson and Memmert, 1991, *Biotechnol. Bioeng.* 38:972–976.
Smiley et al., 1989, *Biotechnol. Bioeng.* 33:1182–1190.
Yang et al., 1995, *Cancer Res.* 55:4210–4213.
Al–Rubeai et al., 1992, *Cytotechnology* 9:85–97.
Barak et al., 1993, *EMBO J.* 12:461–468.
Bebbington et al., 1992, *Bio/Technology* 10:169–175.
Belsham and Sonenberg, 1996, *Microbiological Reviews* 60:499–511.
Berger et al., 1988, *Gene* 66:1–10.
Boise et al., 1993, *Cell* 74:597–608.
Cherbonnel–Lasserre et al., 1996, *Oncogene* 13:1489–1497.
Chiou et al., 1994, *Molecular and Cellular Biology* 14:2556–2563.
Coats et al., 1996, *Science* 272:877–880.
Cockett et al., 1990, *Bio/Technology* 8:662–667.
Crameri et al., 1996, *Nature Biotechnology* 14:315–319.
Crook et al., 1994, *Cell* 79:817–827.
Datto et al., 1995, *Proc. Natl. Acad. Sci. U.S.A.* 92:5545–5549.
Davies and Kaufman, 1992, *J. Virol.* 66:1924–1932.
Dirks et al., 1994, *Gene* 149:387–388.
Dirks et al., 1993, *Gene* 128:247–249.
Duke et al., 1992, *J. Virol.* 66:1602–1609.
El–Deiry et al., 1993, *Cell* 75:817–825.
Ewen et al., 1995, *Genes Dev.* 9:204–217.
Flores–Rozas et al., 1994, *Proc. Natl. Acad. Sci. U.S.A.* 91:8655–8659.
Gartenhaus et al., 1996, *Proc. Natl. Acad. Sci. U.S.A.* 93:265–268.
Gill and Ptashne, 1988, *Nature* 334:721–724.
Gossen and Bujard, 1992, *Proc. Natl. Acad. Sci. U.S.A.* 89:5547–5551.
Gu et al., 1993, *Biotechnol. Bioeng.* 42:1113–1123.
Harper et al., 1993, *Cell* 75:805–816.
Hayter et al., 1991, *Appl. Microbiol. Biotechnol.* 34:559–564.
Heim et al., 1995, *Nature* 373:663–664.
Huang et al., 1997, *Oncogene* 14:405–414.
Itoh et al., 1995, *Biotechnol. Bioeng.* 48:118–122.
Jackson et al., 1990, *TIBS* 15:477–483.
Jenkins and Hovey, 1993, *Biotechnol. and Bioeng.* 42:1029–1036.
Kaminski et al., 1990, *EMBO J.* 9:3753–3759.
Kaufman et al., 1991, *Nucleic Acids Res.* 19:4485–4490.
Kim et al., 1992, *Mol. Cell Biol.* 12:3636–3643.
Kim, 1998, *Biotechnol. and Bioeng.* 58:65–72.
Kirchhoff et al., 1995, *Oncogene* 11:439–445.
Ko and Prives, 1996, *Genes Dev.* 10:1054–1072.
Köster et al., 1995, "Animal Cell Technology:Developments Towards the 21st Century," 33–43.
Kuerbitz et al., 1992, *Proc. Natl. Acad. Sci. U.S.A.* 89:7491–7495.
Lane, 1992, *Nature* 358:15–16.
Lee et al., 1996, *Biotech. Bioeng.* 50:273–279.
Lees et al., 1992, *Genes Dev.* 6:1874–1885.
Lin et al., 1992, *Proc. Natl. Acad. Sci. U.S.A.* 89:9210–9214.
Linke et al., 1996, *Genes Dev.* 10:934–947.
Macejak and Sarnow, 1991, *Nature* 353:90–95.
Minn et al., 1996, *Genes and Dev.* 10:2621–2631.
Mitchell et al., 1991, *Cytotechnology* 5:223–231.
Murray et al., 1996, *Biotechnol. Bioeng.* 51:298–304.
No et al., 1996, *Proc. Natl. Acad. Sci. U.S.A.* 93:3346–3351.
Pagano et al., 1992, *Science* 255:1144–1147.

(List continued on next page.)

*Primary Examiner*—David Guzo
(74) *Attorney, Agent, or Firm*—Pennie & Edmonds LLP

(57) ABSTRACT

Provided by the invention are novel methods, vectors and cells for the recombinant production of desired gene products. In particular, the invention relates to increased production of desired gene products by inducibly arresting cell proliferation. The invention also provides novel multicistronic expression vectors that are useful not only for recombinant gene expression, but also for other applications such as gene therapy, tissue engineering and metabolic engineering.

37 Claims, 11 Drawing Sheets

OTHER PUBLICATIONS

Figure 1:
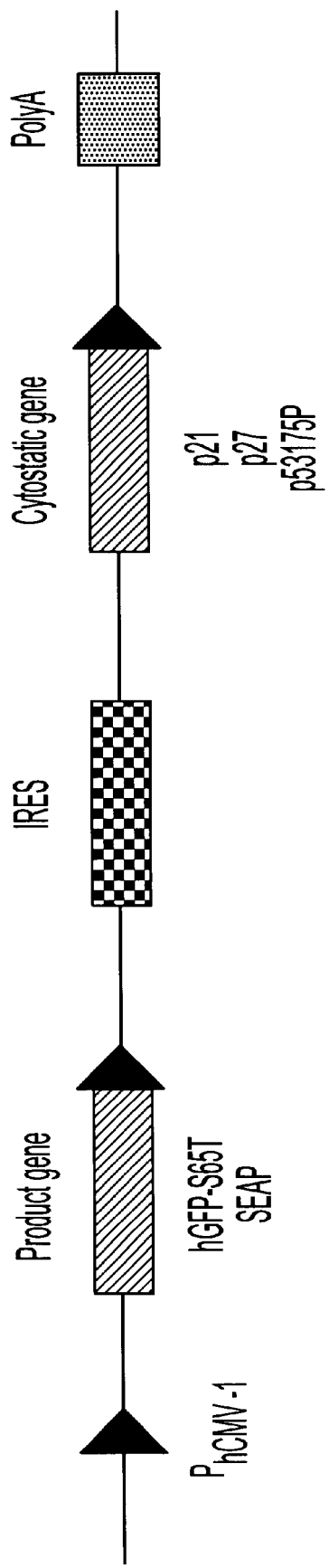

Paulus et al., 1996, *J. Virol. 70:*62–67.
Pendse et al., 1992, *Biotechnol. Bioeng. 40:*119–129.
Pine, 1992, *J. Virol. 66:*4470–4478.
Pines, 1994, *Nature 369:*520–521.
Polyak et al., 1994a, *Cell 78:*59–66.
Polyak et al., 1994b, *Gene and Dev. 8:*9–22.
Polyak et al., 1996, *Genes Dev. 10:*1945–1952.
Ptashne and Gann, 1990, *Nature 346:*329–331.
Rees et al., 1996, *BioTechniques 20:*102–110.
Renner et al., 1995, *Biotech. Bioeng. 47:*476–482.
Reynisdottir et al., 1995, *Genes and Dev. 9:*1831–1845.
Rowan et al., 1996, *EMBO J. 15:*827–838.
Schultze et al., 1996, *Nat. Biotechnol. 14:*499–503.
Sekiguchi and Hunter, 1998, *Oncogene 16:*369–380.
Shaw et al., 1992, *Proc. Natl. Acad. Sci. U.S.A. 89:*4495–4499.
Sherr, 1994, *Cell 79:*551–555.
Shocket et al., 1995, *Proc. Natl. Acad. Sci. U.S.A. 92:*6522–6526.
Singh et al., 1996, *Biotechnol. Bioeng. 52:*166–175.
Smith et al., 1994, *Science 266:*1376–1380.
Sugimoto et al., 1994, *Bio/Technology 12:*694–698.
Suzuki and Ollis, 1990, *Biotechnol. Prog. 6:*231–236.
Symonds et al., 1994, *Cell 78:*703–711.
Tanaka et al., 1996, *Nature 382:*816–818.
Timchenko et al., 1996, *Genes & Dev. 10:*804–815.
Tonouchi et al., 1992, *J. Biotechnol. 22:*283–290.
Toyoshima and Hunter, 1994, *Cell 78:*67–74.
Triezenberg et al., 1988, *Genes Dev. 2:*718–729.
Tsujimoto and Croce, 1986, *Proc. Natl. Acad. Sci. U.S.A. 83:*5214–5218.
Waga et al., 1994, *Nature 369:*574–578.
Wertz and Hanley, 1996, *TIBS 21:*359–364.
Windle et al., 1991, *Genes Dev. 5:*160–174.
Xiong et al., 1993a, *Nature 366:*701–704.
Xiong et al., 1993b, *Genes Dev. 7:*1572–1583.
Yonish–Rouach et al., 1991, *Nature 352:*345–347.

CYTOSTATIC PROCESS INCREASES THE PRODUCTIVITY OF CULTURED CELLS

1. FIELD OF THE INVENTION

The invention is in the field of recombinant gene expression technology. In particular, the invention relates to methods, vectors and cells for the recombinant production of desired gene products. The invention also provides novel multicistronic expression vectors that are useful not only for recombinant gene expression, but also for other applications such as gene therapy, tissue engineering and metabolic engineering.

2. BACKGROUND OF THE INVENTION

Most cell lines used for recombinant protein production are chosen based on their ability to proliferate indefinitely. Robust cell growth is essential to clone good producers and to propagate such clones to a high cell density in the production process. Additionally, many previous studies have reported a positive correlation between growth rate and product formation (Smiley et al., 1989, Biotechnol. Bioeng. 33:1182–1190; Cockett et al., 1990, Bio/Technology 8:662–667; Hayter et al., 1991, Appl. Microbiol. Biotechnol. 34:559–564; Robinson and Memmert, 1991, Biotechnol. Bioeng. 38:972–976; Pendse et al., 1992, Biotechnol. Bioeng. 40:119–129), while only few investigations have reported the opposite (Mitchell et al., 1991, Cytotechnology 5:223–231; Bebbington et al., 1992, Bio/Technology 10:169–175; Tonouchi et al., 1992, J. Biotechnol. 22:283–290).

The phenomenon that reduced specific growth rate may increase cell culture productivity of the cell has been observed with hybridoma cells producing monoclonal antibodies (Mab's) (Suzuki and Ollis, 1990, Biotechnol. Prog. 6:231–236; Al-Rubeai et al., 1992, Cytotechnology 9:85–97). However, since in these and other experiments, the G1-arrest of the cell cycle is achieved by starvation of the cells for an essential nutrient or energy source or by the addition of DNA synthesis inhibitors such as thymidine or hydroxyurea, TGF-β (Suzuki and Ollis, 1990, supra; Al-Rubeai et al., 1992, supra) or genotoxic agents such as adriamycin (Gartenhaus et al., 1996, Proc. Nate. Acad. Sci. 93:265–268), such processes are not preferred for use in prolonged production phases since these approaches interfere with cell viability and/or disturb metabolic processes necessary for protein synthesis (Marcus et al., 1985, Ann. Rev. Genet. 19:389–421; Windle et al., 1991, Genes Dev. 5:160–174; Di Leonardo et al., 1993, Cold Spring Harbor Symp. Quant. Biol. 58:655–667; Wertz and Hanley, 1996, TIBS 21:359–364, for a review).

The first relevant biotechnological contribution to protein production in proliferation-inhibited cells came from the isolation of a temperature-sensitive CHO cell line. These mutants showed 3 to 4 times higher production of a tissue inhibitor of metalloproteinases (TIMP) when growth arrest was induced by a temperature shift to 39° C. (Jenkins and Hovey, 1993, Biotechnol. and Bioeng. 42:1029–1036). Although the productive life span of the cells was extended in arrested cultures and the overall productivity was higher, the mutant cells showed a rapid decrease in viability upon prolonged exposure to elevated temperatures. Thus, while temperature-dependent growth control can be an attractive approach from a process viewpoint, potential problems include not only viability loss at elevated temperatures but also potential lower productivity at suboptimal temperatures.

Most successful cell culture processes make use of proliferating cells. Inevitably, proliferation beyond a certain desired cell density causes nutrient and oxygen depletion, accumulation of lactate and other toxic products, and deterioration and degradation of the product. Much efforts are devoted to improve positive control of cultured cell proliferation, e.g., by replacing the growth factor-containing animal serum by more sophisticated, better-defined technologies which involve use of defined chemical media with defined protein additives and/or adaptation of cell lines, or their genetic engineering, to permit growth in low- or no-protein medium (Renner et al., 1995, Biotech. Bioeng. 47:476–482; Lee et al., 1996, Biotech. Bioeng. 50:273–279). For example, engineering cells to overexpress survival genes from the bcl-2 family, such as bcl-2, bcl-$x_L$ and E1B, has been used for higher robustness and obviation of the cellular death program in production. (Boise et al., 1993, Cell 74:597–608; Chiou et al., 1994, Molecular and Cellular Biology 14:2556–2563; Itoh et al., 1995, Biotechnol. Bioeng. 48:118–122; Cherbonnel-Lasserre et al., 1996, Oncogene 13:1489–1497; Han et al., 1996, Genes and Dev. 10:461–477; Murray et al., 1996, Biotech. Bioeng. 51:298–304; Singh et al., 1996, Biotechnol. Bioeng. 33:1182–1190; Huang et al., 1997, Oncogene 14:405–414).

Production using growing cells contrasts with the natural situation in which many cells of a mature mammal display no further growth after terminal differentiation yet continue to produce and often secrete proteins during the lifetime of the organism. In an intact mammalian organism, uncontrolled proliferation is detrimental and can result in tumor production.

Many proteins which inhibit proliferation have emerged from cancer research where the absence or mutation of the respective genes corresponds to a state of uncontrolled proliferation and cancerous growth. Such genes are referred to as tumor suppressor genes. The p53 tumor suppressor gene is the most commonly mutated gene in human cancer, with the majority of mutations being amino acid substitutions (Lane, 1992, Nature 358:15–16; Greenblatt et al., 1994, Cancer Res. 54:4855–4878; Ko and Prives, 1996, Genes Dev. 10:1054–1072).

The normal role of p53 is to induce cell-cycle arrest predominantly at the G1-checkpoint in response to DNA damage by binding to damaged DNA in a non-specific fashion via its C-terminal domain (Kastan et al., 1991, Cancer Res. 51:6304–6311). p53 has also been implicated as a general metabolic sensor (Linke et al., 1996, Genes Dev. 10:934–947). The G1-checkpoint control function is executed by accumulation of p53 followed by the site-specific binding to promoter elements and corresponding induction of the MDM2, GADD45, IGF-BP3 and p21 genes (Kastan et al., 1991, supra; Barak et al., 1993, EMBO J. 12:461–468; El-Deiry et al., 1994, Cancer Res: 54:1169–1174).

Induction of p53 leads not only to cell growth arrest but also to programmed cell death, or apoptosis, under some conditions. Both the cytostatic and apoptosis mechanisms enable p53 to control DNA damage by protecting cellular descendants from accumulating excessive mutations (see Ko and Prives, 1996, supra, for a review). The molecular process determining whether cells subjected to genotoxic stress arrest their growth for subsequent repair of DNA damage or undergo apoptosis is poorly understood. The overall response to p53 expression varies among different cell lines (Yonish-Rouach et al., 1991, Nature 352:345–347; Shaw et al., 1992, Proc. Natl. Acad. Sci. 89:4495–4499; Liu et al., 1994 and 1995, Cancer Res. 54:3662–3667, 55:3117–3122; Symonds, et al., 1994, Cell 78:703–711; Yang et al., 1995a, Cancer Res. 55:4210–4213; Polyak et al., 1996, Genes Dev. 10:1945–1952). Recently, a p53 mutant designated p53175P has been isolated from a cervical carcinoma (Crook et al., 1994, Cell 79:817–827); this mutant showed a specific loss of apoptotic but not cell-cycle arrest function (Rowan et al., 1996, EMBO J. 15:827–838).

p21, another tumor suppressor gene, inhibits DNA replication and enhances DNA repair by interaction with the replication and repair factor, the proliferating cell nuclear antigen designated PCNA (Xiong et al., 1993a and b, Nature 366:701–704, Genes Dev. 7:1572–1583; Flores-Rozas, et al., 1994, Proc. Natl. Acad. Sci. 91:8655–8659; Smith et al., 1994, Science 266:1376–1380; Waga et al., 1994, Nature 369:574–578). At high concentrations, p21 also inhibits the function of cyclin-dependent kinases (Cdks), particularly those that function during the G1-phase of the cell cycle (Gu et al., 1993a, Biotechnol. Bioeng. 42:1113–1123; Harper et al., 1993, Cell 75:805–816; Xiong et al., 1993a, supra). These Cdks normally phosphorylate the product of the retinoblastoma tumor suppressor gene (Rb) in a cyclin-dependent manner which subsequently activates the E2F family of transcription activators and eventually leads to cell-cycle progression and the beginning of S-phase (Pagano et al., 1992, Science 255:1144–1147; Lees et al., 1992, Genes Dev. 6:1874–1885).

Besides activation by p53, p21 can also be induced by the CCAAT/enhancer-binding protein α (C/EBPα) as part of the cell-cycle inhibition program following terminal differentiation (Timchenko et al., 1996, Genes & Dev. 10:804–815). Additionally, C/EBPα stabilizes p21 at the protein level and increases thereby its half-life (Timchenko et al., 1996, supra). Recently, it has also been reported that mutant fibroblast cells lacking a functional interferon responsive factor gene (IRF-1) do not express p21 following cytotoxic stress (Tanaka et al., 1996, Nature 382:816–818). IRF-1 is a DNA-binding transcription activator which accumulates in response to interferons and leads to the general antiviral state of the cells (Pine 1992, J. Virol. 66:4470–4478). Regulated overexpression of IRF-1 was shown to reversibly control proliferation in mammalian cells (Köster et al., 1995, in "Animal Cell Technology: Developments Towards the 21st Century", pp. 33–43, E. C. Beuvery et al. (eds.), Kluwer Academic Publ., Dordrecht, The Netherlands), but, unlike p21, IRF1-mediated growth arrest does not lead to the inhibition of proliferation at a specific cell cycle phase (Kirchhoff et al., 1995, Oncogene 11:439–445). Additionally, induction of IRF-1 leads to a decrease in cell viability and a decrease in production of a marker gene unless that marker gene is placed under the direct transcriptional regulation of the IRF-1 DNA binding factor (Kbster et al., supra).

Another pathway, which is p53-independent, blocks the mammalian cell cycle in G1 in response to the antimitogenic cytokine called transforming growth factor-β (TGF-β). p27, a cyclin-dependent kinase inhibitor (Cdi) is responsible for this cell-cycle block (Coats et al., 1996, Science 272:877–880). p27 and p21 are highly homologous in their N-terminus, suggesting that they may bind and inhibit cyclin-Cdk complexes in a similar fashion (Polyak et al., 1994a, Cell 78:59–66; Toyoshima and Hunter, 1994, Cell 78:67–74). However, p21 and p27 differ in their affinity for different Cdks; p21 binds most tightly to Cdk2, whereas p27 binds with more affinity to Cdk4 (Polyak et al., 1994a, supra). Moreover, unlike p21, which is primarily regulated at the level of transcription, the level of p27 mRNA and protein remains the same in quiescent and proliferating cells, and throughout the cell cycle (Toyoshima and Hunter, 1994, supra). p27 is regulated through binding a heat-labile "masking" factor, and is unmasked when cells are treated with TGF-β, or become contact-inhibited (Polyak et al., 1994b, Gene and Dev. 8:9–22; Sherr, 1994, Cell 79:551–555). Recently, p21 has also been shown to be induced by TGF-β and to cooperate with Ink4 Cdk inhibitors to induce p53-independent cell-cycle arrest (Datto et al., 1995, Proc. Natl. Acad. Sci. 92:5545–5549; Reynisdottir et al., 1995, Genes and Dev. 9:1831–1845). However, p53 can also indirectly interfere with Cdk4 inhibition by repressing translation of the respective mRNA (Ewen et al., 1995, Genes Dev. 9:204–217).

3. SUMMARY OF THE INVENTION

The invention provides methods and compositions for achieving a cell culture production process that combines rapid growth to the desired cell density followed by a production phase with little or no proliferation. Unencumbered by demands for simultaneous production of cellular proteins and all other cellular components, the protein synthesis apparatus and all of the metabolic activity of the cell can be mobilized and devoted entirely to production of the desired recombinant protein in this proliferation-inhibited state.

In one of its aspects, the invention provides a method for increasing production of any desired product, and particularly protein products, from a cultured cell. The method comprises culturing a cell under conditions such that expression of a tumor suppressor gene product that blocks the cell cycle is induced and cell proliferation arrested, and collecting the product from the cultured cell. Preferred tumor suppressor gene products are p53, p21 and p27. In one aspect, expression of the tumor suppressor gene is achieved by transforming the cell with a recombinant polynucleotide vector encoding the tumor suppressor gene under the control of an inducible promoter.

An advantageous embodiment of this method involves coexpressing in the cultured cell both the inducible tumor suppressor gene and an antiapoptosis gene, for example, bcl-2 and bcl-$x_L$. Yet another embodiment of the method entails coexpressing both the inducible tumor suppressor gene and a factor that stabilizes the tumor suppressor gene product in the cell. These embodiments find particular use in methods of production using stably transformed cells.

The invention also encompasses mammalian cells that have been genetically engineered to express both a desired product gene and to inducibly express a tumor suppressor gene, mammalian cells genetically engineered to express an antiapoptosis gene and to inducibly express a tumor suppressor gene, and mammalian cells genetically engineered to inducibly express a tumor suppressor gene and/or to express a factor that stabilizes the tumor suppressor gene product in the cell.

The invention also provides a number of novel vector systems. In one aspect, there is provided a recombinant polynucleotide vector comprising an inducible promoter, a sequence encoding a product protein, and a sequence encoding a tumor suppressor gene product that is operatively linked to the inducible promoter. In an embodiment of this vector, the inducible promoter is also operatively linked to the sequence encoding the protein product by expressing both coding sequences cocistronically. Translation of one of the coding sequences is cap dependent, while translation of the other coding sequence is controlled by an internal ribosomal entry site.

Still another aspect of the invention are recombinant polynucleotide vectors comprising a promoter operably linked to an expression cassette containing at least three cistrons. Translation of the second, third and any additional cistrons is directed by internal ribosomal entry sites.

In yet another aspect, the invention provides recombinant polynucleotide vectors comprising an inducible promoter operatively linked to an expression cassette. The expression cassette comprises at least two cistrons and translation of the second cistron is directed by an internal ribosomal entry site. Additionally, the expression cassette encodes a positive regulator of the inducible promoter. Induction of the promoter leads to a positive auto regulated cascade of high level expression.

The invention also encompasses host cells containing the novel vectors of the invention.

4. BRIEF DESCRIPTION OF THE DRAWINGS

FIG. 1. Schematic diagram of a DNA configuration used for dicistronic expression of a model product (green fluorescent protein, hGFP-S65T; secreted alkaline phosphatase, SEAP) together with a cytostatic protein which inhibits cell proliferation (p21, p27, p53175P). The tetracycline-regulatable promoter (PhCMV*-1) allows tetracycline-responsive regulation of a single mRNA which can be translated to give both the product and the cytostatic proteins. The intervening internal ribosomal entry site (IRES) of picornaviral origin ensures the cap-independent translation of the second cistron whereas the first relies on classical cap-dependent translation-initiation. The polyadenylation site is derived from the SV40 virus.

Figure 2:
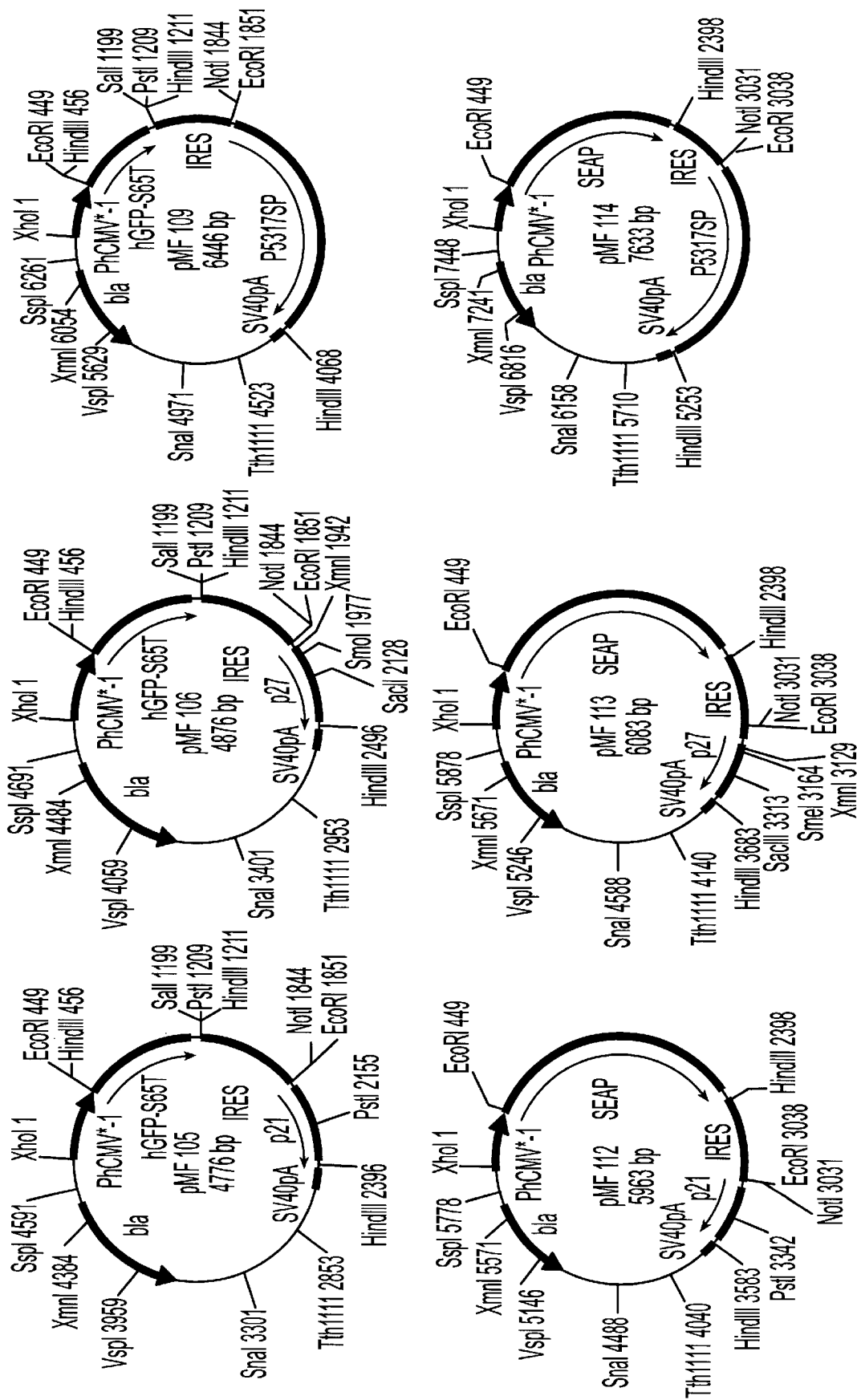

FIG. 2. Dicistronic expression vectors harboring the polyadenylation site from the SV40 virus, the ampicillin gene (bla), and the tetracycline-responsive promoter PhCMV*-1 driving the dicistronic expression unit. The dicistronic expression unit contains the model product genes encoding a derivative of the green fluorescent protein (hGFP-S65T) or the secreted alkaline phosphatase (SEAP) and the cytostatic, cell-cycle arresting genes encoding the cyclin-dependent kinase inhibitors, p21 or p27, or p53175P, a mutant of the tumor suppressor gene p53.

Figure 3:
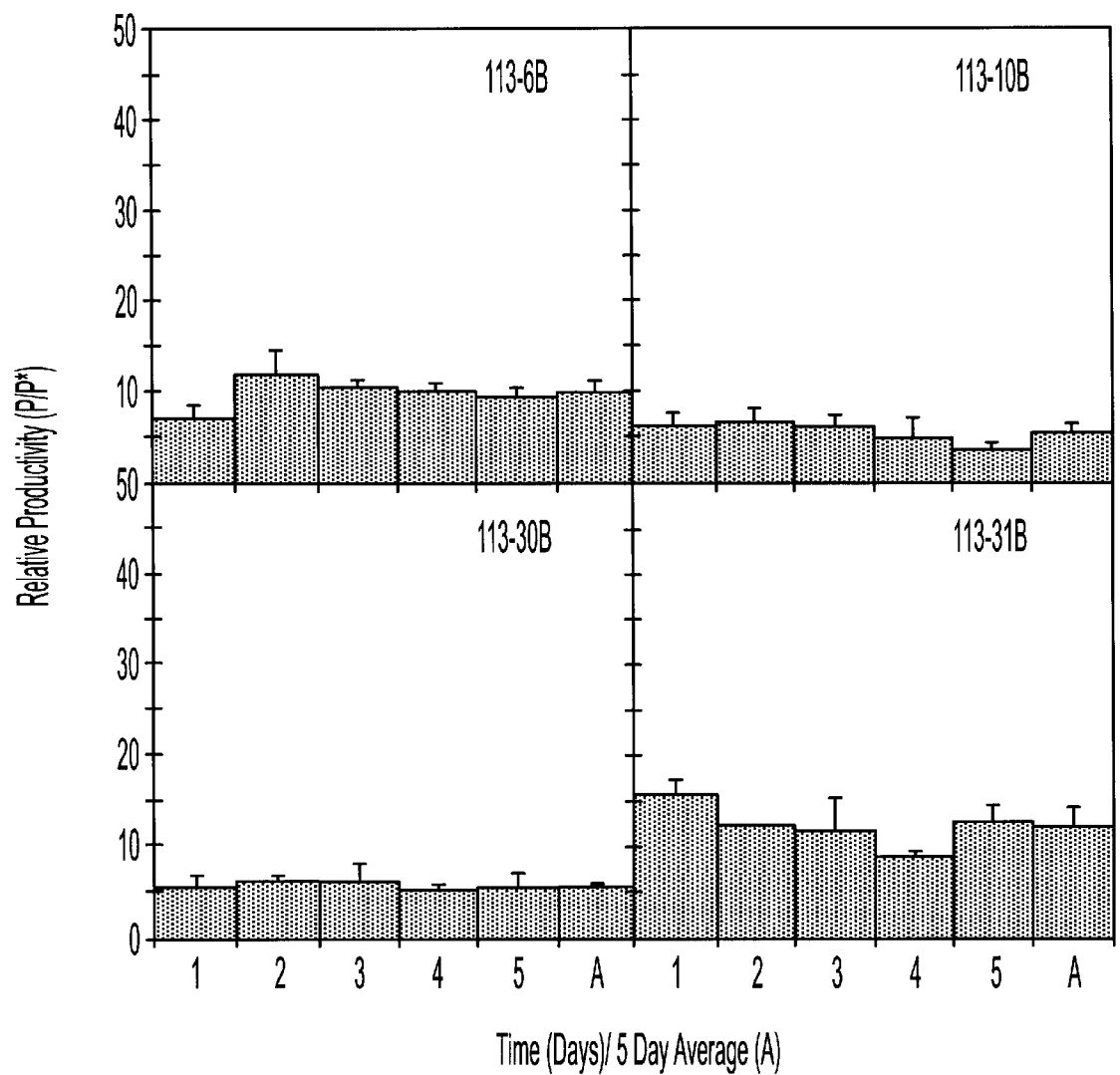

FIG. 3. SEAP productivity of proliferation-inhibited clones 113-6B, 113-10B, 113-30B, and 111-31B. The per cell SEAP productivity of growth-arrested clones (P) relative to the per cell SEAP productivity of the control cells (111-10; P*) is shown over a period of five days. The productivity factor (P/P*) indicates the relative higher SEAP production of individual proliferation-inhibited cells compared to their proliferation-competent counterpart 110-10 at a particular timepoint. A represents the average relative per cell productivity (P/P*) over the whole production period of five days.

FIG. 4. Maps of the tricistronic expression vectors: FIG. 4A—pTRIDENT1 and pTRIDENT3; FIG. 4B—pTRIDENT2 and pTRIDENT4; and FIG. 4C—pTRIDENT7 and pTRIDENT8. The plasmids contain a high copy number pBluescript®-based vector backbone including the ori and the beta-lactamase-encoding gene (bla) conferring ampicillin resistance in E. coli. As promoters, the tetracycline-regulatable PhCMV*-1, the ecdysone-responsive promoter PEC (Invitrogen) or the SV40 promoter/enhancer sequences (SV40 P/E) are used along with the splice donor and splice acceptor of the 19S mRNA of SV40 Vp2. Whereas IRES I and IRES II are identical fragments of the poliovirus 5' non-translated region extending from nucleotide 1 to 628 (Sarnow, 1989), IRES-EV contains the corresponding genetic element of the encephalomyocarditis virus which was mutated for enhanced translation efficiency. The polyadenylation signal (pA) is derived from SV40.

Figure 5:
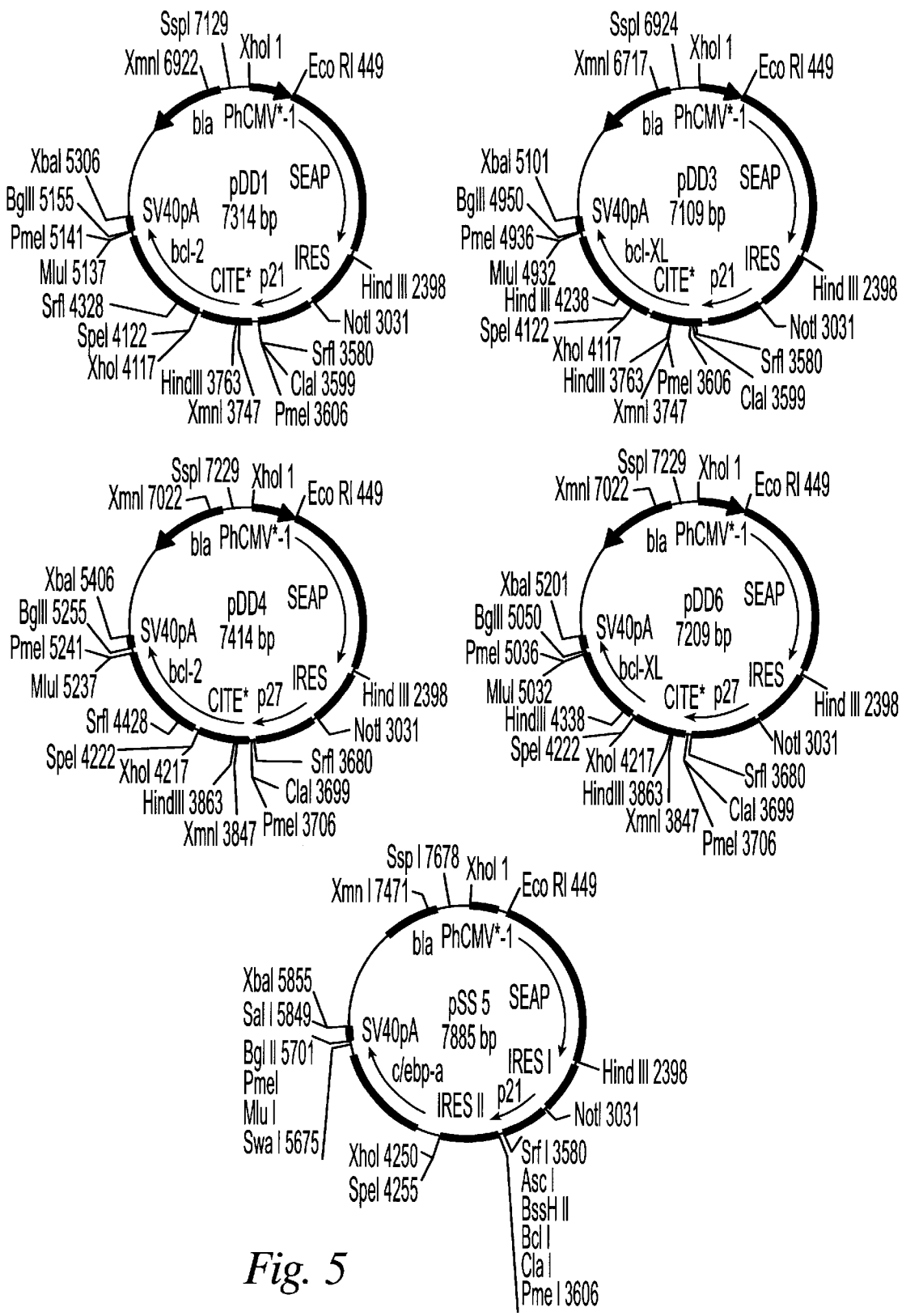

FIG. 5. Maps of the tricistronic expression vectors pDD1, pDD3, pDD4, pDD6, and pSS5.

Figure 6:
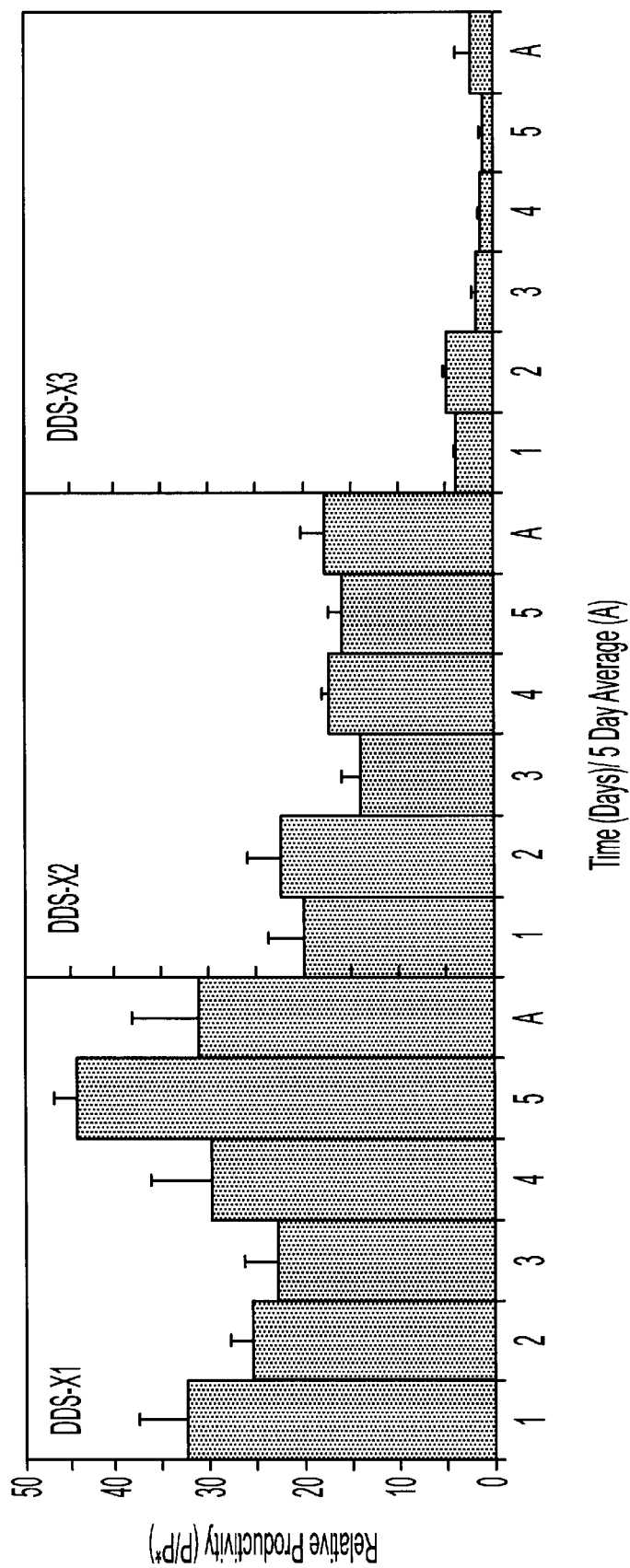

FIG. 6. SEAP productivity of growth-arrested cells harboring pDD6. The SEAP productivity (P/P*) (on a per cell basis) of growth-arrested CHO cells that express SEAP, p27 and bcl-$x_L$ in a tricistronic manner is shown over a period of five days. Data for three CHO cell lines, DD6-X1, DD6-X2, and DD6-X3 is shown. Cell lines DD6-X2 and DD6-X1 display an 18 to 30 times higher relative SEAP productivity (P/P*) when compared to the control cell line 111-10.

Figure 7:
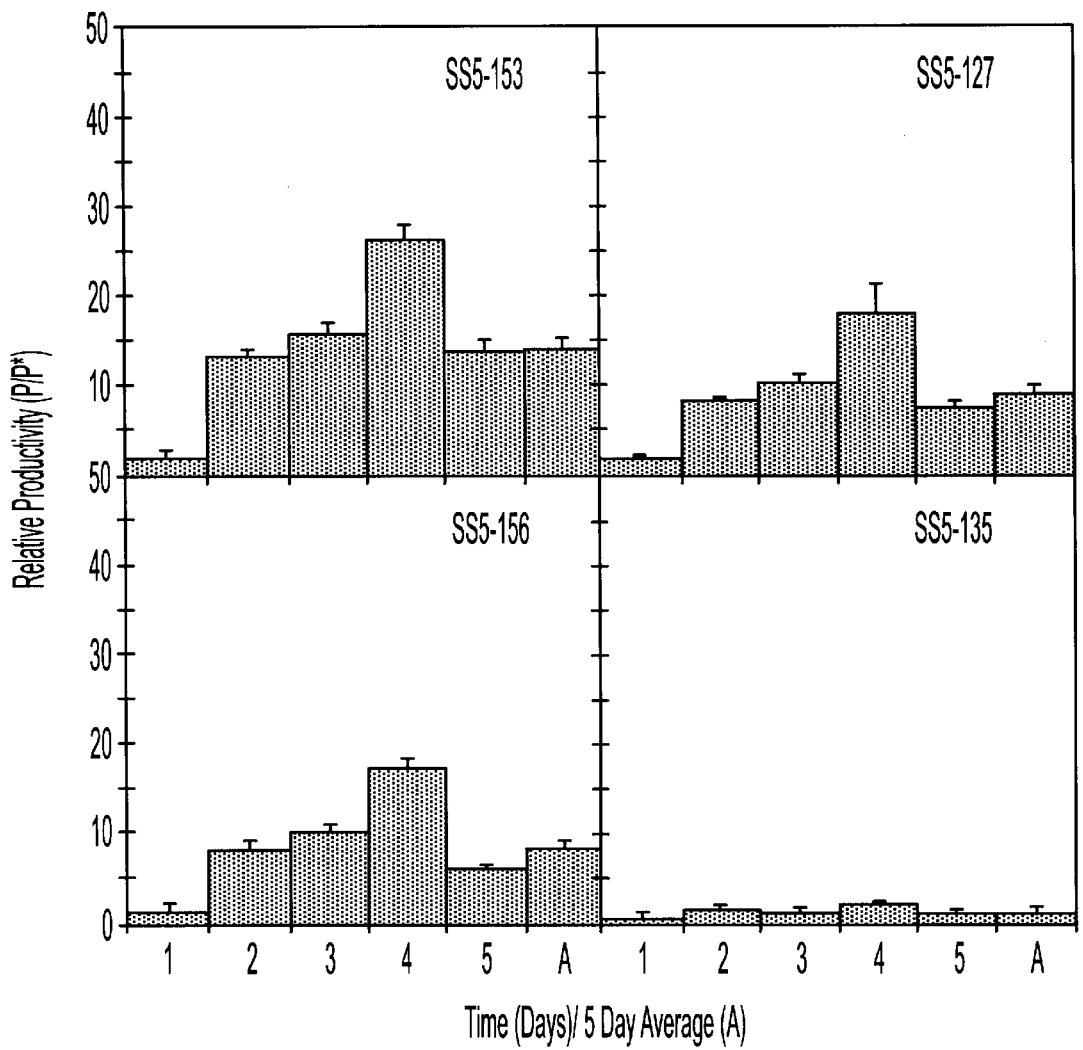

FIG. 7. Relative SEAP productivity of SS5-153, SS5-127, SS5-156, and SS5-135. Under growth-arrested conditions, cell lines SS5-127, SS5-156, and SS5-153 produce 10 to 15 times more SEAP on a per cell basis than the control cell line 111-10.

Figure 8:
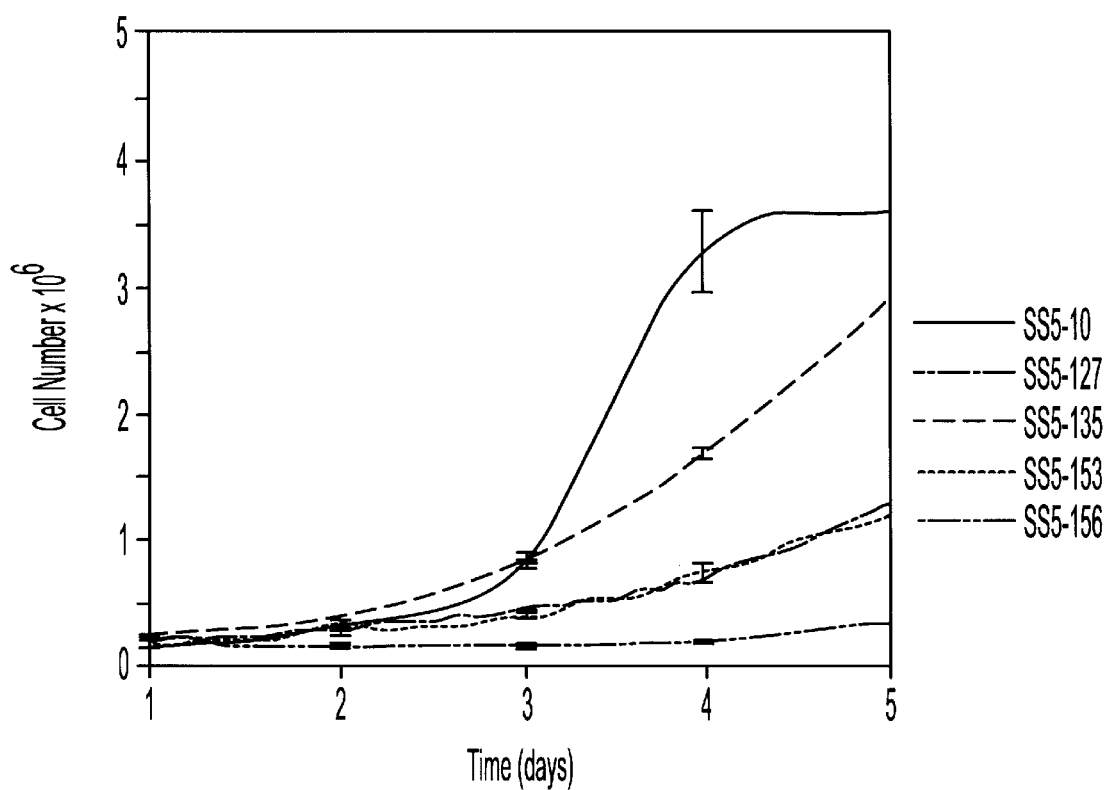

FIG. 8. Proliferation Potential of XMK1–9 Cells Stably Transfected With pSS5. When induced, the pSS5 vector directs the expression of p21 and C/EBPα. The control cell line, 111-10, is as described below in the Examples sections. SS5-135, SS5-153, SS5-127, and SS5-156 are different cell lines stably transfected with pSS5. Time in days is measured from the onset of induction.

Figure 9:
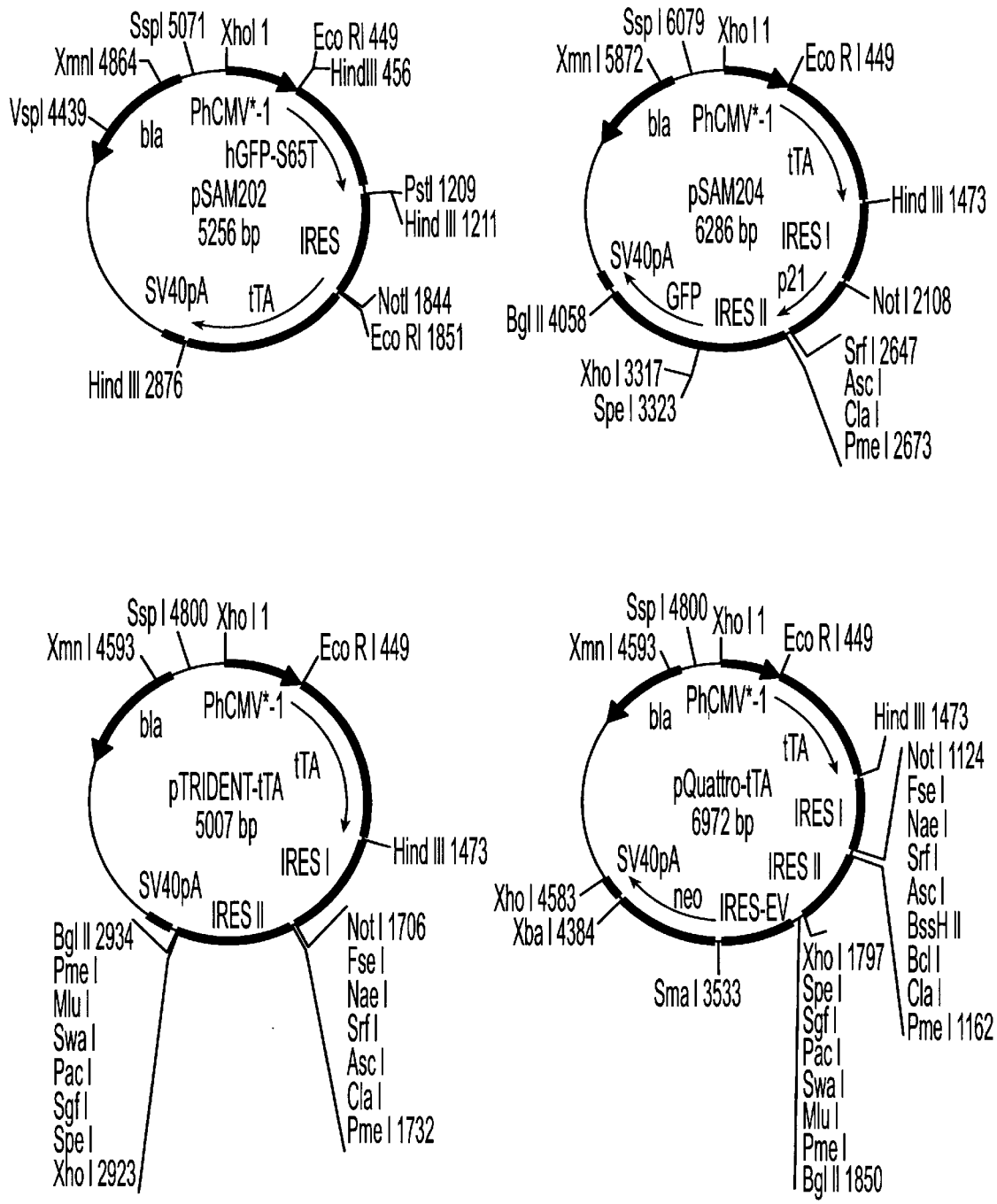

FIG. 9. Autoregulatory Di- and tricistronic expression vectors. All expression vectors harbor the polyadenylation site from the SV40 virus (pA), the gene conferring resistance to ampicillin (bla), and the tetracycline-responsive promoter (PhCMV*-1) which drives transcription of the multicistronic expression unit. pTRIDENT-tTA is a general positive feedback expression vector allowing the insertion of one or two different genes for simultaneous and co-ordinated as well as regulated expression. pQuattro-tTA is isogenic to pTRIDENT-tTA but allows G418 selection since it contains the neomycin resistance downstream of an additional, mutated, cap-independent translation enhancer of the encephalomyocarditis virus (IRES-EV). Besides tTA, GFP-S65T (pSAM202), GFP cycle 3 mutant (pSAM204) and/or the cytostatic gene p21 have been used as model product proteins.

5. DETAILED DESCRIPTION OF THE INVENTION

Cultured cells have long been used as vehicles for the production of cell products of interest. The invention is based, in part, on the discovery that specific expression of tumor suppressor gene products in cultured cells not only arrests cell proliferation, but also significantly increases cell productivity. While arrested, cells remain healthy and retain the ability to proliferate once the induction signal is removed. Thus, the invention takes advantage of both the robust proliferation potential of cells in culture, and the ability to arrest that proliferation at will. This combination of both positive and negative controls of cultured cell proliferation leads to an improved cell culture process in which cells grow as rapidly as possible to high cell density, then enter a production phase in which cell proliferation is arrested. The term "arresting cell proliferation" means that cell division is partially inhibited or completely stopped.

For purposes of the invention, tumor suppressor gene products are intracellular proteins that block the cell cycle at a cell cycle checkpoint by interaction with cyclins, Cdks or cyclin-Cdk complexes, or by induction of proteins that do so. Thus, these tumor suppressor gene products inhibit the cyclin-dependent progression of the cell cycle. Particularly preferred tumor suppressor gene products act on the G1-S transition of the cell cycle. The invention encompasses the use of any tumor suppressor gene product which performs this function, whether known or yet to be discovered. Examples of tumor suppressor genes include p21, p27, p53 (and particularly, the p53175P mutant allele), p57, p15, p16, p18, p19, p73, GADD45 and APC1.

A tumor suppressor gene product can be specifically induced by placing the coding sequence for the tumor suppressor gene under the control of an inducible promoter. An inducible promoter is defined herein, for purposes of the invention, as any promoter whose transcriptional initiation activity can be modified by alteration of conditions external to the cell. Also included within the scope of the invention is that a tumor suppressor gene product can be specifically induced by expression of a cloned gene encoding an activator of expression of a tumor suppressor, or cell cycle arrest, gene.

In another embodiment of the invention, the cell culture production process consisting of a proliferation-inhibited production phase is further refined to express the tumor suppressor gene(s) concomitantly with one or more survival factors. Survival factors are intracellular proteins that prevent apoptosis such as bcl-2, bcl-$x_L$, E1B-19K, mcl-1, crmA, abl, p35, bag-1, A20, LMP-1, Tax, Ras, Rel and NF-κB-like factors. Additionally, all known survival factors, as well as survival factors yet to be discovered, are useful in the methods and compositions of the invention. In yet another embodiment, the tumor suppressor gene(s) is expressed concomitantly with a factor that stabilizes the tumor suppressor gene product in the cell. Examples of stabilizing factors are members of the CAAT enhancer binding protein family. For example, p21 protein activity is stabilized when coexpressed with C/EBPα. Additionally, C/EBPα specifically induces transcription of the endogenous p21 gene. Thus, C/EBPα functions as both a stabilizing factor and as a specific inducer of p21.

The desired gene product may be collected from the cultured cells either during the time cell proliferation is arrested, or after the time of proliferation arrest, using techniques well known to those of skill in the art. Additionally, expression of the desired gene product can be constitutive in the cultured cell, or can be induced concomitantly with induction of tumor suppressor gene product. Production of any gene product may be increased using the compositions and methods of the present invention. For example, production of a marker gene product, such as green fluorescent protein, or of a model secreted gene product, such as SEAP, may be increased. Naturally, the invention finds particular use in the production of products of industrial or pharmaceutical interest such as industrial enzymes (e.g. proteases, cellulases, glycosidases, or ligninases), interferons (e.g. β-INF, α-INF, γ-INF), hGH, insulin, erythropoietin, tissue plasminogen activator (tPA), DNAse, monoclonal antibodies, Factor VIII, Factor VII, Factor IX, HSA, IL-2, glucagon, EGF, GCSF, GMCSF, thrombopoietin, gp160, HbSAg, and other viral antigenic proteins and peptides (rotavirus, HIV, p53ras).

The methods of the invention are useful in cell culture production processes using any type of eukaryotic cell, including but not limited to mammalian cells, insect cells, fungal cells, and reptilian cells.

The invention additionally provides improved vectors that are useful in the cell culture production process of the invention. These improved vectors are also advantageous in any number of other expression system applications, including but not limited to cell culture, coordinated gene product production, gene therapy, metabolic engineering and tissue engineering. The vectors of the invention comprise tricistronic and quattrocistronic expression systems that make use of both cap-dependent translational initiation sites and internal ribosomal entry sites (IRES). Such vectors are surprisingly stable in transformed cells.

In yet another aspect of the invention there is provided recombinant polynucleotide vectors comprising an inducible promoter operatively linked to an expression cassette. The expression cassette comprises at least two cistrons and translation of the second cistron is directed by an internal ribosomal entry site. The expression cassette further encodes a positive regulator of the inducible promoter. Induction of the promoter leads to a positive auto regulated cascade of high level expression.

Such positive autoregulated vectors have a number of important attributes. The vectors allow one to intall in one cloning step a cloned gene with regulated expression which is particularly advantageous for metabolic engineering of a cell line or tissue. Other applications for which these autoregulated vectors can be particularly useful are for regulated expression of a cloned gene product that is inhibitory to its own production, or for production in systems that are much slower to engineer and modify than cell lines such as transgenic animals. For example, the tTA transactivator protein is toxic to cells such as HeLa cells. In order to obtain regulated activation of gene expression unsing the tTA transactivation, tetracyline-off promoter system, one must search through many transfected cell clones to find one that expresses enough tTA protein to provide a reasonable activation of gene expression when tetracycline is withdrawn, but not so much tTA protein as to kill the cells. The autoregulated vectors of the invention avoid this cumbersome screening process and allow the one-step realization of regulated gene expression with the tetracycline regulated system.

The invention is illustrated, in part, below by of specific examples. In an embodiment of the invention, CHO cells were transiently transfected with inducible expression constructs encoding tumor suppressor genes. Upon induction, the cells expressed either p53, p21 or p27 and became growth arrested. Surprisingly, the simultaneous production of model product genes was increased approximately four-fold over non-growth arrested cells.

In another illustration of the invention, CHO cells were stably transfected with the same inducible expression constructs encoding tumor suppressor genes. Induction of the stably transfected p27 gene arrested growth and increased production of a model product gene even further—up to twelve-fold over control cells that did not inducibly express p27. In a refinement of this method, an antiapoptotic gene product, bcl-$x_L$, is coexpressed with p27. Coexpression of the p27 tumor suppressor gene product and the antiapoptotic gene product increases production of a model product gene a further 3 fold, up to 30 fold more than control cells.

In yet another illustration of the invention using stably transfected cell lines, coexpression of the p21 tumor suppressor gene product and the stability factor c/ebpα also resulted in growth arrest and up to ten-fold increased expression of a model product gene over control cell lines that did not coexpress p21 and c/ebpα.

5.1 Methods for Expressing Gene Products, Including Tumor Suppressor Gene Products, In Cells Expression of tumor suppressor gene products, as well as other gene products, may advantageously be achieved by recombinant DNA technology using techniques well known in the art. Such methods can be used to construct expression vectors containing a chosen nucleotide sequence and appropriate transcriptional and translational control signals. These methods include, for example, in vitro recombinant DNA techniques, synthetic techniques, and in vivo genetic recombination. (See generally, Sambrook et al. (1989) *Molecular Cloning* Vols. I-III, Cold Spring Harbor Laboratory Press, Cold Spring Harbor, N.Y., and Ausubel et al., *Current Protocols in Molecular Biology* (1989) John Wiley & Sons, all Vols. and periodic updates thereof, herein incorporated by reference). Alternatively, RNA capable of encoding chosen nucleotide sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

Methods of achieving the expression of tumor suppressor gene products (or other gene products such as antiapoptosis gene products or stability factors) in cultured cells include, but are not limited to, integrating a polynucleotide encoding the gene product into the chromosome of the cell or transforming the cell to carry the gene extrachromasomally.

The particular expression vector systems utilized to express nucleotide sequences encoding tumor suppressor gene products, antiapoptosis gene products and stability factors will depend upon the cell type. Generally, the expression vector will comprise a promoter operably linked to nucleotide sequences encoding the desired gene product and containing a transcriptional initiation sequence, and a transcriptional terminator. The promoter should be one that is transcriptionally active in the cell, and may be inducible or constitutive. The gene product encoded by the expression vector may be one that naturally occurs in the cell, or may be from a different cell type or species.

The expression construct should also encode appropriate recognition sequences for translational initiation in the cell. Optionally, the expression construct may contain signals for intracellular targeting of the gene product. For example, nuclear localization of a translational gene product may be increased by methods that are known to those of skill in the art. Finally, the vector may be designed for extrachromosomal maintenance, or for recombination into the chromosome.

Appropriate promoter sequences, transcriptional and translational initiation sequences, and terminators for a given host cell are well known. Expression vectors for various hosts, such as plants, mammalian cells, insect cells, *E. coli*, Bacillus, and fungi (including Saccharomyces, Aspergillus, and Penicillium) are well known to those of ordinary skill in the art. Further, illustrated below by way of working examples are additional expression vectors appropriate for expression in mammalian cells.

Preferred promoters for use in achieving cytostasis are regulatable or inducible promoters. Known inducible mammalian promoters are the promoters of heat shock proteins (Schwienfest et al., 1988, Gene 71, 207–210), metallothionein-regulated promoters (Hu and Davidson, 1990, Mol. Cell. Biol. 10, 6141–6151), and steroid-regulated promoters (Israel and Kaufman, 1989, Nucl. Acids. Res. 12, 4589–4604; Ko et al., 1989, Gene 84, 383–389). Still other regulatable systems are based on fusions of heterologous proteins with the ligand-binding domains of several members of the steroid hormone receptor family (e.g., estrogen receptor, ER), which renders the fusion protein regulatable by the cognate hormone (e.g., estrogen derivatives; Mattioni et al., 1994, Methods Cell Biol. 43, 335–352).

In particular embodiments of the invention (illustrated below by way of examples) the promoters rely on bacterial systems adapted for use in eukaryotic cells. Examples of such promoters include the tetracycline-repressible promoter PhCMV*-1 (Gill and Ptashne, 1988, Nature 334, 721–724; Gossen and Bujard, 1992, Proc. Nat. Acad. Sci. USA 89:5547–5551), the recently described ecdysone-regulated promoter which allows adjustable gene expression in response to this insect hormone and its derivatives (No et al. 1996, Proc. Natl. Acad. Sci. USA 93, 3346–3351; Invitrogen), and the IPTG-responsive promoter (Baim et al., 1991, Proc. Natl. Acad Sci. USA 88,5072–5076; Fieck et al., 1992, Nucl. Acids. Res. 20, 1785–1791). The invention also encompasses modified versions of these promoter systems. For example, several genetic variations of the tTA system, and combinations with other regulation systems, are known such as: (i) fusion of tTA with the ligand-binding domain of the estrogen receptor (tTAER; Iida et al., 1996, J. Virol. 70, 6054–6059); (ii) fusion of tTA with a nuclear localization signal gives tight regulation and high level induction of the reporter gene (Yoshida and Hamada, 1997, Biochem. Biophys. Res. Comm 230, 426–430); (iii) regulation of the lacI repressor by the tetracycline-regulatable system produces a regulatory cascade (Aubrecht, et al., 1996, Gene 172, 227–231); and (iv) construction of different tTA responsive promoters by fusion of the tet operators to various minimal promoters (Hoffmann et al, 1997, Nucl. Acids. Res. 25, 1078–1079).

Alternatively, inducible expression of a tumor suppressor gene, or other gene, may be achieved by altering expression of a gene endogenous to the cell. As an example, homologous recombination may be used to replace an endogenous promoter with another more transcriptionally active promoter or an inducible promoter of choice. Transcription may also be transactivated by inserting a transcriptional enhancer adjacent the endogenous gene, or by increasing the activity of transcriptional enhancers.

5.2 Methods Of Introducing Polynucleotides Into Host Cells

The invention also pertains to a host cell transfected with polynucleotides containing the tumor suppressor genes operatively linked to an inducible promoter, and host cells transfected with the vectors of the invention. Such host cells may be maintained in culture or may be part of an animal, such as a mammal. Polynucleotides of interest are typically inserted into any of a wide range of vectors as described above which are subsequently delivered using the presently disclosed methods and materials.

5.2.1 Cultured Cells

Host cells for use with the methods and vectors of the invention may be any prokaryotic or eukaryotic cell. As noted above, ligating the polynucleotide into a gene construct, such as a vector, and transforming or transfecting into host cells, either eukaryotic (yeast, avian, insect or mammalian) or prokaryotic (bacterial cells) are standard procedures used widely in the microbial or tissue-culture technologies. Preferred mammalian host cultured cell types for the methods and vectors of the invention include but are not limited to CHO, BHK, HeLa, PLC, Jurkat, HT-1080, Hep G2, ECV304, COS-7, NIH/3T3, HaCat, LCL, HUVEC, NSO and HL60.

Vectors suitable for cultivation of the subject polynucleotides in bacterial cells, such as *E. coli*, include plasmids of the types: pBR322-derived plasmids, pEMBL-derived plasmids, pEX-derived plasmids, pBTac-derived plasmids, and pUC-derived plasmids. For replication in yeast, the YEP24, YIP5, YEP51, pYES2 and YRP17 plasmids are cloning and expression vehicles useful in the introduction of genetic constructs in *S. cerevisiae* (see, for example, Broach et al., 1993, in *Experimental Manipulation of Gene Expression*, ed. M. Inouye, Academic press, p. 83). These vectors can replicate in both *E. coli* due to the presence of the pBR322 ori, and in yeast due to the replication determinant of the yeast 2 $\mu$m circle plasmid. In addition, drug resistant markers such as ampicillin can be used.

Similarly, preferred mammalian vectors for the polynucleotides of the invention contain also prokaryotic sequences to facilitate the propagation of the vector in bacteria. Such vectors, when transfected into mammalian cells, can be designed to integrate into the mammalian chromosome for long term stability by use of a linked selectable marker gene or by use of retroviral sequence signals. A number of different mammalian expression vectors are commercially available from, for example, Promega (Madison, Wis.) and Stratagene (La Jolla, Calif.). Alternatively, derivatives of viruses such as the bovine papillomavirus (BPV-1) or Epstein-Barr virus can be used for transient expression. The various methods employed in the preparation of plasmid transformation of host organisms are well known in the art. For other suitable vector systems, as well as general recombinant procedures, see Sambrook et al., supra.

5.2.2 Gene Therapy

The invention also encompasses the use of the vectors of the invention in gene therapy. For gene therapy purposes, expression constructs of the instant invention may be administered in any biologically effective carrier, e.g., any formulation or composition capable of effectively delivering the recombinant gene to cells in vivo. Approaches include construction of the subject vectors as viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example cationic polymers, cationic liposomes (e.g. lipofectin, cholesterol derivatives such as D.D.A.B. and cationic phospholipids) or derivatized (e.g., antibody conjugated), polylysine conjugates, gramicidin S, artificial viral envelopes or other such intracellular carriers, as well as direct injection of the naked gene construct, electroporation or CaPO$_4$ precipitation carried out in vivo. A recent review of gene transfer and expression systems for cancer gene therapy is Cooper, 1996, Seminars in oncology 23:172–187.

It will be appreciated that because transduction of appropriate target cells represents a first step in gene therapy, choice of the particular gene delivery system will depend on such factors as the phenotype of the intended target and the route of administration, e.g. locally or systemically. Target cells include but are not limited to hematopoietic cells, hepatocytes, epithelial cells, myoblasts, myocytes, lymphocytes and keratinocytes. Furthermore, it will be recognized that the particular gene construct provided for in vivo transduction of expression constructs are also useful for in vitro transduction of cells, such as for use in the ex vivo tissue culture systems described above.

A preferred approach for in vivo introduction of nucleic acid into a cell is by use of a viral vector containing nucleic acid, e.g., a particular multicistronic expression vector. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid. Suitable vectors which can be delivered using the presently disclosed methods and compositions include, but are not limited to, herpes simplex virus vectors, adenovirus vectors, adeno-associated virus vectors, retroviral vectors, pseudorabies virus, alpha-herpes virus vectors, and the like. A thorough review of viral vectors, particularly viral vectors suitable for modifying nonreplicating cells, and how to use such vectors in conjunction with the expression of polynucleotides of interest can be found in the book *Viral Vectors: Gene Therapy and Neuroscience Applications* Ed. Caplitt and Loewy, Academic Press, San Diego (1995).

It has been shown that it is possible to limit the infection spectrum of viruses and consequently of viral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al., 1989, PNAS 86:9079–9083; Julan et al., 1992, J. Gen. Virol. u3:3251–3255; and Goud et al., 1983, Virology 163:251–254); or coupling cell surface receptor ligands to the viral env proteins (Neda et al., 1991, J. Biol. Chem 266:14143–14146). Coupling can be in the form of the chemical cross-linking with a protein or other variety (e.g. lactose to convert the env protein to an asialogycoprotein), as well as by generating fusion proteins (e.g. single-chain antibody/env fusion proteins). For example, cancer cells may be targeted using this technique by, for example, coupling antibodies against tumor-associated molecules or cancer cell surface proteins to the surface of the recombinant virus. This technique, while useful to limit or otherwise direct the infection to certain tissue types, can also be used to convert an ecotropic vector into an amphotropic vector.

A preferred viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al., 1988, BioTechniques 6:616; Rosenfeld et al., 1991, Science 252:431–434; and Rosenfeld et al., 1992, Cell 68:143–155. Suitable adenoviral vectors derived from the adenovirus strain AD type 5 d1324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including airway epithelium (Rosenfeld et al., 1992, cited supra.), endothelial cells (Lemarchand et al., 1992, Proc. Natl. Acad Sci. USA 89:6482–6486), hepatocytes (Herz and Gerard, 1993, Proc. Natl. Acad. Sci USA 90:2812–2816) and muscle cells (Quantin et al., 1992, Proc. Natl. Acad. Sci USA 89:2581–2584). Furthermore, the virus particle is relatively stable, amenable to purification and concentration, and can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., cited supra, Haj-Ahmand and Graham, 1986, J. Virol. 57:267). Most replication-defective adenoviral vectors currently in use and therefore favored by the present invention are deleted for all or part of the viral E1 and E3 genes but retain as much as 80% of the adenoviral genetic material (see, e.g., Jones et al., 1979, Cell 16:683; Berkner et al., supra; and Graham et al. in Methods in Molecular Biology, E. J. Murray, Ed. (Humana, Clifton N.J., 1991) vol. 7, pp. 109–127).

Another viral vector system useful for delivery of one of the vectors of the invention is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., 1992, Curr. Topics in Micro. and Immunol. 158:97–129). It is also one of the few viruses that may integrate its DNA into non-dividing cells, and exhibits a high frequency of stable interaction (see for example Flotte et al., 1992, Am. J. Respir. Cell. Mol. Biol. 7:349–354; Samulski et al., 1989, J. Virol. 63:3822–3828; and McLaughlin et al., 1989, J. Virol. 63:1963–1973). Vectors containing as little as 300 base pairs of AAV can be packaged and can integrate. Space for exogenous DNA is limited to about 4.5 kb. An AAV vector such as that described in Tratschin et al., 1985, Mol. Cell. Biol. 5:3251–3260 can be used to introduce DNA into cells. A variety of nucleic acids have been introduced into different cell types using AAV vectors (see for example Hermonat et al., 1984, Proc. Natl. Acad. Sci USA 81:6466–6470; Tratschin et al., 1985, Mol. Cell. Biol. 4:2072–2081; Wondisford et al., 1988, Mol. Endocrinol. 2:32–39; Tratschin et al., 1984, J. Virol. 51:611–619; and Flotte et al., 1993, J. Biol. Chem. 268:3781–3790).

In addition to viral transfer methods, such as those illustrated above, non-viral methods can also be employed to cause transfer of the vectors of the invention in the tissue of an animal. Most nonviral methods of gene transfer rely on normal mechanisms used by mammalian cells for the uptake and intracellular transport of macromolecules. In preferred embodiments, non-viral gene delivery systems rely on endocytic pathways for the uptake of the subject expression constructs by the targeted cell. Exemplary gene delivery systems of this type include liposomal derived systems, poly-lysine conjugates, and artificial viral envelopes.

In clinical settings, the gene delivery systems for therapy can be introduced into a patient by any of a number of methods, each of which is well known in the art. For instance, a pharmaceutical preparation of the gene delivery system can be introduced systemically, e.g. by intravenous injection, and specific expression of the construct in the target cells occurs predominantly from specificity of transfection provided by cell-type or tissue-type expression due to the promoter sequences included on the vector, or the promoter sequences in combination with the gene delivery vehicle targeting particular cell types. In other embodiments, initial delivery of the recombinant expression construct is more limited with introduction into the animal being quite localized. For example, the gene delivery vehicle can be introduced by catheter (see U.S. Pat. No. 5,328,470) or by stereotactic injection (e.g. Chen et al., 1994, PNAS 91:3054–3057). A vector of the invention can be delivered in a gene therapy construct by electroporation using techniques described, for example, by Dev et al., 1994, Cancer Treat. Rev. 20:105–115.

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells which produce the gene delivery system.

5.3 Novel Multicistronic Vectors For Use in the Invention

5.3.1 Tricistronic and Quattrocistronic Vectors

The invention also provides, in an another aspect, a novel family of multicistronic vectors that allow the simultaneous cloning and expression of at least three different gene products.

The multicistronic vectors of the invention comprise a promoter operably linked to a transcription unit. Within the transcription unit are at least three independent multiple cloning sites (MCS). Coding sequences of interest may be inserted independently into each MCS. Translational initiation signals, also known as internal ribosomal entry sites (IRES), are included upstream of each MCS. Thus, at least three different cistrons may be expressed. Surprisingly, translational expression of inserted coding sequences is relatively insensitive to the position of the cistron on the transcribed RNA. For example, as described below by way of example, no significant difference was found between expression in the first cistron (cap-dependent) and second cistron (cap-independent). Even the genes encoded by the third cistron was only 2-fold lower than that expressed by the cap-dependent cistron.

Numerous examples of IRES are well known in the art; IRES's have been described in retroviral, yeast, Drosophila, Xenopus and even human mRNAs such as Pip, fibroblast growth factor 2 and cap-binding protein eIF4G, any of which can be used in the invention. Preferred IRES sequences for use in the vectors and methods of the invention are the picornoviral IRES elements. The IRES elements preceding the second and third MCS may be the same IRES element, or they may be different. Although multicistronic vectors containing two copies of the same IRES have been found stable in both prokaryotic cells used for cloning and in mammalian tissue culture cells, it may be advantageous in certain applications (such as targeted homologous recombination) to minimize the possibility of homologous recombination within the multicistronic vectors.

Since expression from the third or last cistron is somewhat less than the first and second cistrons, the last cistron can be used to express a gene product whose expression should be lower. For example, in a particularly advantageous embodiment of the multicistronic vectors of the invention, the third or fourth cistron is used to express a selectable marker gene product. Selection for increased expression of the selectable gene product will concurrently increase expression of the gene products encoded by the first and second cistrons.

5.3.2 Autoregulated Multicistronic Expression Vectors

Another aspect of the invention is inducible, autoregulated expression plasmids. Generally, these vectors contain an inducible promoter operably linked to a sequence that encodes a positive transactivator for the inducible promoter. Because of natural leakiness of the promoter, some transcripts that encode the positive transactivator will originate. In the absence of induction however, these transcripts remain at a low basal level. When the promoter is activated, the positive transactivator is expressed and amplified via a positive feedback regulation system. Preferably, the expression constructs are multicistronic. Activation and positive feedback of the inducible promoter/transactivator system will also activate expression of linked cistrons. Therefore, the inducible promoter/transactivator system finds particular use in conjunction with the multicistronic vectors of the invention.

Illustrated below by way of working examples are inducible promoter/transactivator systems that use the tetracycline-based tTA-PhCMV*-1 elements. However, the novel combination of autoregulation of gene activator expression with multicistronic gene expression technology presented here are not restricted to the tTA-PhCMV*-1 elements employed in these particular vectors. This new strategy can obviously be employed with other regulatory genes and regulated promoters such as the recently described ecdysone-responsive expression system by No et al. (1996), supra., the metallothionein-regulated promoter, any steroid-regulated promoter, and the heat-shock regulated promoter, as well as other inducible promoter systems yet to be described.

The multicistronic, positive feedback regulation vectors of the invention are a useful tool which could significantly contribute to and speed up research focusing on combinatorial effects of different genes and/or multifaceted processes in mammalian cells. Their intrinsic autoregulation system should also enhance their applicability to the creation of disease models for the testing of therapeutic agents and to efforts to understand the development of mammalian organisms. Furthermore, the expression vectors described here allow "three-in-one" step metabolic engineering of animal cells without the need for subsequent rounds of transfection and selection. Multiple rounds of transfection and selection increase not only the risk of undesired position effects by constructs stably integrated into the chromosome and but also require the maintenance of selective pressure with several compounds which may lower the cost-efficiency of large scale applications. Additionally, the multicistronic and autoregulated vectors of the invention can be used in gene therapy applications, tissue engineering, and cell therapies (for recent reviews on tissue engineering, see Science, Apr. 4, 1997, vol. 276, pp. 60–87).

The invention having been described, the following examples are offered by way of illustration and not limitation.

6. EXAMPLE

Construction of Dicistronic Vectors That Coexpress a Heterologous Gene Product and a Tumor Suppressor Gene The basic monocistronic expression vectors pTBC-1 and pSBC-2 (Dirks et al., 1993 and 1994, Gene 128:247–249, 149:387–388) were used to clone the production reporter genes GFP (GFP-S65T, Clontech laboratories, Palo Alto, Heim et al., 1995, Nature 373:663–664) and SEAP (Berger et al., 1988, Gene 66:1–10) or the cytostatic tumor suppressor genes p21, p27 and p53175P, respectively. The fusion of two monocistronic expression vectors via NotI/VspI generates a dicistronic expression unit which allows the correlated expression of both the model product as well as the cytostatic gene from a single mRNA transcribed under control of the tetracycline regulatable promoter PhCMV*-1 (Gossen and Bujard, 1992, Proc. Natl. Acad. Sci. 89:5547–5551; see FIGS. 1 and 2).

pMF102: The humanized GFP was amplified from phGFP-S65T (Clontech laboratories, Palo Alto; Heim et al., 1995, supra) with oligos OMF27: GATCGAATTCGACCG-GAAGCTTGCCGCC (SEQ ID NO:1) and
OMF36: GATCGTCGACTTACTTGTACAGCTCGTCC (SEQ ID NO:2).

The resulting PCR fragment was cloned via the restriction sites EcoRI/SalI contained in the extensions of the oligos into the corresponding sites of pTBC-1 (Dirks et al., 1994, supra).

pMF111: Plasmid pSBC2-SEAP (Dirks et al., 1993, supra) was restricted with EcoRI and HindIII, and the gene encoding the secreted alkaline phosphatase (SEAP, Berger et al., 1988, supra) was cloned into pTBC-1 via EcoRI/HindIII.

p21 was amplified from pBSSK-/p21 (El-Deiry et al., 1993, Cell 75:817–825) with oligos OMF28: GATCGAAT-TCTTCGCCGAGGCACCGAGG (SEQ ID NO:3) and OMF29: GATCAAGCTTTTAGGGCTTCCTCTTGGAG (SEQ ID NO:4) and ligated via EcoRI/HindIII sites contained in the extensions of the oligos to the corresponding sites of pSBC-2, resulting in plasmid pMF98. Similarly, pMF99 was constructed by cloning p27 amplified with primers OMF30: GATCGAATTCGCGGTCGTGCAGAC-CCGG (SEQ ID NO:5) and OMF31: GATCAAGCTTT-TACGTTTGACGTCTTCTG (SEQ ID NO:6) from pBluescriptIISK-hp27FL (Polyak et al., 1994, supra) into pSBC-2 via the EcoRI/HindIII sites contained in the extensions of the oligos. The correct cloning of p21 and p27 was confirmed by DNA sequence analysis.

The p53 mutant p53175P contained in plasmid pCB6 (Rowan et al., 1996, supra.) was cut out using restriction enzymes EcoRI/BamHI, and ligated to the corresponding sites of pSBC-2 to give pMF96.

Generally, the dicistronic expression vectors were cloned by combining the NotI/VspI fragments of pMF102 and pMF111 containing the production reporter genes GFP and SEAP with the corresponding NotI/VspI fragments of vectors harboring p21 (pMF98), p27 (pMF99) or p53175P (pMF96), respectively (FIG. 2). Thereby, both cistrons are fused in a single transcriptional unit and are independently translated either by cap-dependent (first cistron, product gene) or cap-independent, IRES-mediated (internal ribosomal entry site) (second cistron, cytostatic gene). The following dicistronic expression systems were constructed by the combination of monocistronic expression vectors (FIG. 2): pMF105: pMF102/pMF98 (GFP-p21); pMF106: pMF102/pMF99 (GFP-p27); pMF109: pMF102/pMF96 (GFP-p53175P); pMF112: pMF111/pMF98 (SEAP-p21); pMF113: pMF111/pMF99 (SEAP-p27); pMF114: pMF111/pMF96 (SEAP-p53175P).

7. EXAMPLE

Cell Growth Arrest and Increased Production of Heterologous Gene Product in Cells Transiently Transfected With Dicistronic vectors That Coexpress a Heterologous Gene Product and a Tumor Suppressor Gene

7.1 Material and Methods 7.1.1 Cell Culture and Transfection

Chinese hamster ovary cells (CHO-K1, ATCC: CCL 61) were cultured in FMX-8 medium (Dr. F. Messi Cell Culture Systems, Switzerland) supplemented with 10% fetal calf serum (FCS, Boehringer Mannheim). The cell line XMK1–9, a derivative of CHO-K1 constitutively expressing the tetracycline-responsive transactivator tTA, was cultured in FMX-8 medium that also contained 400 μg/ml of G418 (GIBCO BRL, Life Technologies). For repression of the tetracycline regulatable promoter PhCMV*-1 (Gossen and Bujard, 1992, supra.), 5 μg/ml of tetracycline (Sigma) was used. For high efficiency transfection, a CaPO4 protocol was used yielding an optimized transfection rate of XMK1–9 cells (30% to 50% confluent) of over 30%. The transfected subpopulations expressing the green fluorescent protein (GFP-S65T, Clonetech laboratories, Palo Alto, Heim et al., 1995, supra.) were routinely sorted by FACS as described before (Cheng et al., 1996, Biotechnology 14:606–609; Levy et al., 1996, Nature Biotechnology 14:610–614).

7.1.2 Immunofluorescence

Dicistronic expression vectors were checked for high level expression of the cytostatic genes p21, p27 and p53175P. XMK1"9 cells were transfected as described above and grown on chamber slides (Lab-Tek, Nunc, Inc.) for 48 h to allow expression and adaptation. The cell monolayer was washed once with phosphate buffered saline (PBS) and submerged with 3% paraformaldehyde solution in PBS for 15 to 30 min. XMK1"9 cells were then washed again with PBS and submerged with 0.2% Triton X-100 for 10 min. After another washing step, the cells were immersed in 2% BSA in PBS for 15 min. and subsequently incubated 1 hour with a 1:50 dilution of the corresponding antibodies. Antibodies specific for p21 (rabbit polyclonal WAF1/Cip1 (C19) cat# sc-397, lot# G284) or for p27 (rabbit polyclonal (M-197) cat# sc-776, lot# B065) were purchased from Santa Cruz Biotechnology Inc., and the anti-p53 antibody was purchased from Oncogene (monoclonal (Ab-1) cat# opo3, lot# 39930101). Thereafter, the antibody solutions were discarded and the fixed cells were washed three times for 5 min. with PBS before the second antibodies (anti-rabbit or anti-mouse, Pierce or Capple) conjugated to Texas Red were applied for 1 hour. Cells were then fixed with Lisbeth's embedding medium (7 ml 100% glycerol, 3 ml 0.1 M Tris-HCL pH 9.5; 0.5 g n-propyl-galate (Sigma #P3130) and examined under the fluorescence microscope (Leica, Leitz DMRB). Particular care regarding the timing of the overall process and the incubation times with Triton-X had to be taken whenever coexpression of p21, p27 and p53175P with GFP was monitored, since GFP rapidly leaks out of the cells even when fixed with BSA and Lisbet.

7.1.3 Flow Cytometry and Cell-cycle Analysis

Transfected CHO cells were grown for 48 h to about 80% to 90% confluence prior to FACS analysis. The cells were detached with dissolvation solution (Sigma), and diluted in PBS to a concentration of $\sim 1 \times 10^6$/ml. optionally, for cell-cycle analysis and sorting of G1-arrested cells, 10 µl of Hoechst 33342 solution (Sigma, 1 mg/ml in H2O) was added per 1 ml of cells and incubated for 1 hour at 37° C. Total populations were gated to remove doublets and very small debris as well as dead cells and gated for high GFP fluorescence. Cells falling in this region were analyzed separately for their cell-cycle position using Hoechst 33342-mediated fluorescence. All FACS analyses were performed on a FACStarPlus (Becton-Dickinson, San Jose, Calif.).

7.1.4 SEAP Assay

500 µl of culture medium of a specific population were heated for 5 min. at 65° C. After 2 min. of centrifugation at 14000×g, up to 160 µl of the supernatant were transferred to a 96 well plate containing 40 µl of 5×SEAP assay buffer (5 M diethanolamine pH 9.8; 2.5 mM $MgCl_2$, 50 mM L-homoarginine). Water was added to a final volume of 200 µl. The total sample was prewarmed to 37° C. for 10 min. Prior to the reaction, 20 µl of prewarmed 120 mM p-NPP (p-nitrophenolphosphate in 1×SEAP buffer) was added. The increase in light absorbance was measured at 405 nm at appropriate time intervals at 37° C. (adapted from Berger et al., 1988, supra). The relative slope of such a light absorbance time course of an individual cell population containing a dicistronic expression vector versus the one harbouring the control plasmid pMF111 was used as a direct measure for the SEAP production of a particular cell population. Since all cell populations consisted of the same number of cells after FACS-mediated sorting and since all subpopulations harbored the same overall amount of SEAP-encoding, dicistronic expression vectors (or the control plasmid, respectively) as judged by the identical mean green fluorescence of selected subpopulations, these data could be directly compared. Generally, subpopulations were grown for up to two days after FACS-mediated selection before SEAP production was quantified. Although the control cells of the control population resume proliferation during this time the overall SEAP-producing potential this population does not change as the SEAP expression vectors are distributed to the daughter cells. Certainly, the intracellular plasmid concentration of the proliferation-competent control cells decreases over time but the productivity of the whole population remains constant.

7.1.5 Colony Growth Assay

The cell line XMK1–9, a derivative of CHO-K1 (ATCC: CCL 61) expressing the tetracycline regulation transactivator (tTA, Gossen and Bujard, 1992, supra), was transfected with pMF105, pMF106 and pMF109 coexpressing GFP together with the cytostatic genes p21, p27 and p53175P from dicistronic constructs (FIG. 2). The mixed cell population was grown for 48 h. The transfected population, apparent by the expression of GFP, was subsequently sorted by FACS as described above. This selected subpopulation was further grown for another 48 hours attached to a pretreated glassplate of a perfusion chamber (POC chamber #0727.000, Bachofer, Reutlingen, FRG). The ratio of growing versus arrested cells was subsequently determined by counting a total of 500 cells for each cell population harbouring a different dicistronic expression vector. Cell division becomes apparent after 48 hours as proliferation competent cells begin to form microcolonies whereas cell-cycle arrested cells remain single.

7.2 Results

7.2.1 CHO Cells Transiently Transfected with Dicistronic Expression Vectors Coexpress Functionally Active Cytostatic Genes p21, p27 and p53175P Together with the Model Product Genes hGFP-S65T and SEAP In order to achieve a tightly linked as well as controlled expression of a product gene and a cytostatic gene, we generated several dicistronic expression vectors (FIGS. 1 and 2). Translation of both the product gene and the cytostatic gene was under the control of PhCMV*-1, the tetracycline regulatable promoter by Gossen and Bujard (1992), supra. Both genes are separated by a short picornaviral element, the internal ribosomal entry site (IRES), which allows cap-independent translation of the second cistron containing the cytostatic gene (FIGS. 1 and 2). The simultaneous and correlated expression of the model product genes concomitant with the cytostatic genes could readily be examined following transient transfections of the dicistronic expression vectors containing various combinations of GFP or SEAP with p21, p27, and p53175P into XMK1–9, a tetracycline regulatable transactivator (tTA)-expressing CHO cell line. In general, transfected populations were examined 48 h after transfection. Expression of GFP was examined by fluorescence microscopy and FACS analysis; production of SEAP was monitored by an enzymatic assay quantifying the amount of alkaline phosphatase secreted by the transfected subpopulation.

Overexpression of the cytostatic genes p21, p27 and p53175P from the dicistronic vectors was about 10-fold above the background level of non-transfected cells as judged by immunofluorescence. Examination of dicistronic constructs combining these cytostatic genes with the expression of GFP showed a strict correlation of green fluorescence with the overexpression of p21, p27 and p53, respectively. However, in rare cases, individual cells of a cell population transfected with p21-containing dicistronic expression vectors showed enhanced expression of p21 in the absence of GFP. These cells were different in morphology compared to the GFP-p21 coexpressing cells and are reminiscent of senescent, non-transfected cells which have been reported to naturally up-regulate p21 expression.

7.2.2 The Coexpression of the Genes Encoded by the Dicistronic Expression Unit is Strictly Regulated by Tetracycline The regulatability of the PhCMV*-1 promoter driving the dicistronic expression unit was assessed by fluorescence microscopical examination of XMK1–9 cells transfected with dicistronic, GFP-encoding expression vectors (FIG. 2) or with the isogenic control vector pMF102. Transfected cells were grown in perfusion chambers which allow rapid addition or removal of tetracycline via the perfused medium. Starting with a period of two days in tetracycline-free medium following transfection, the medium conditions were alternately changed with respect to tetracycline every other day for a total of 8 days. Green fluorescence could only be observed, as could overexpression of the cytostatic genes, when the cells were grown in tetracycline-free medium. Furthermore, division of cells displaying high green fluorescence under tetracycline-free conditions could only be observed to occur in phases when tetracycline was added to the culture medium (see below). The presence of tetracycline prevents binding of tTA to PhCMV*-1 and abolishes transcription of the dicistronic expression unit. Consequently, GFP and the cytostatic gene is no longer overexpressed and cell cycling is resumed. Since the detection of green fluorescence is very sensitive and since GFP accumulates intracellularly, we observed better repression of GFP expression at a tetracycline concentration of 5 $\mu$g/ml in the medium than with 2 $\mu$g/ml as originally described (Gossen and Bujard, 1992, supra).

7.2.3 Tetracycline-regulated Expression of the Cytostatic Genes Inhibits Cell Proliferation and Arrests CHO Cells in the G1-phase The anti-proliferative, cytostatic effect of the tumor suppressor genes p21, p27 and p53 or p53175P has been previously reported for various cell lines (El-Deiry et al., 1993, supra; Polyak et al., 1994, supra; Toyoshima and Hunter 1994, supra; Rynisdottir et al., 1995, supra; Coats et al., 1996, supra; Linke et al., 1996, supra; Polyak et al., 1996, supra; Rowan et al., 1996, et al.). In order to quantify the anti-proliferative potential of the above mentioned tumor suppressor genes expressed from dicistronic constructs in CHO cells, we sorted GFP expressing cells by FACS two days after they had been transfected with the dicistronic vectors pMF105 (GFP-p21), pMF106 (GFP-p27) and pMF109 (GFP-p53175P) and the isogenic control plasmid pMF102 (GFP). FACS analysis of transfected populations revealed that neither the expression of GFP nor the expression of the cytostatic genes changed the intrinsic cell parameters such as cell size and cell shape. Therefore a standard gate could be set which selected single, viable cells prior to analysis of green and DNA fluorescence. Since all cell populations transfected with dicistronic expression vectors showed also a similar two-dimensional FACS profile monitoring green fluorescence versus DNA fluorescence, identical FACS parameters were applied to select subpopulations arrested in G1-phase of the cell cycle. This guaranteed the reproducible selection of subpopulations showing a distinct range of intensities of green fluorescence. Due to the dicistronic nature of the expression plasmids, the intensity of green fluorescence directly correlates with the amount of the cytostatic protein produced. The combined use of FACS sorting and dicistronic expression produces highly consistent and comparable data resulting from experiments with different anti-proliferative genes without the risk of observing only clonal differences of stably selected cell lines.

After having been sorted by FACS, cell populations harboring pMF105, pMF106, pMF109 or pMF102 were subsequently seeded into perfusion chambers which allowed observation of individual cells and the determination of the duration of the induced growth arrest. As determined by microscopical examination of green fluorescence and immunofluorescence intensities of selected, non-proliferating cell populations, there was a clear correlation of the growth inhibitory potential of a particular cytostatic gene and the amount of that gene expressed, or, equivalently in these constructs, the intensity of the green fluorescence observed. We examined in detail the proliferative potential of the subpopulation with high GFP expression (ranging from $10^2$ to $10^4$ GFP fluorescent units in the FACS assay). Whereas about 80% of the cells in sorted subpopulations harboring pMF105, pMF106 or pMF109 remained completely arrested two days after FACS selection (thus a total of 4 days following transfection), 90% of the control cells harboring pMF102 were still able to divide. Table 1 shows the data obtained from the visual examination under the fluorescence microscope of 500 individual clones for each expression vector.

TABLE 1

Cytostatic potential of dicistronic expression vectors

| transfected vector | genetic determinants | proliferating cells |
| --- | --- | --- |
| pMF102 | hGFP-S65T | 87% ± 6% |
| pMF105 | hGFP-S65T, p21 | 18% ± 8% |
| pMF106 | hGFP-S65T, p27 | 27% ± 5% |
| pMF109 | hGFP-S65T, p53175P | 17% ± 9% |

Although the growth arrest was generally very stable for almost 8 days, with some individual cells being arrested for more than 10 days, proliferation resumed thereafter, although at a significantly lower rate. Since the resumption of cell cycling correlated with a decrease in the green fluorescence, it could be a consequence of breakdown of the transfected plasmid DNA rather than a general adaptation of the cells in response of overexpression of the cytostatic gene.

During the phase of growth inhibition, the cells remained proliferation competent and re-entered cell cycle after cessation of p21, p27 or p53175P production following the addition of tetracycline. This indicates that growth-inhibited cells remain viable, which is consistent with our data based on microscopical observations that arrested cells do not die by either necrosis or apoptosis. Presumably as a consequence of the overexpression of the cytostatic genes and the subsequent growth arrest, the transfected cells, most prominently the ones expressing p53 or p21, became round and remained only loosely attached to the culture vessel and to neighboring cells. The round shape of the cells is highly indicative of an imminent doubling of the chromosome and entrance into S-phase. However, arrested cells do not enter S-phase and their nuclear membranes remain intact.

In order to provide evidence that CHO cells overexpressing p21, p27 or p53l75P are arrested in the G1-phase of the cell cycle, as has been previously shown for many other cell lines (Kastan et al., 1991, supra; Kuerbitz et al., 1992, Proc. Natl. Acad. Sci. USA 89:7491–7495; Lin et al., 1992, Proc. Nat. Acad. Sci. 89:9210–9214; Harper et al., 1993, supra; Xiong et al., 1993, supra; Di Leonardo, 1994; Pines, 1994, Nature 369:520–521; Polyak et al., 1994, supra; Toyoshima and Hunter, 1994, supra; Coats et al., 1996, supra; Rowan et al., 1996, supra), we stained the cells transfected with pMF105, pMF106 and pMF109 with the fluorescent DNA binding dye Hoechst 33342 prior to FACS analysis. A two-dimensional analysis of the GFP and Hoechst 33342 fluorescence revealed an exclusive arrest of the manipulated cells in the G1 phase of the cell cycle. The extent of cell-cycle arrest was greater for higher GFP expression, and consequently for higher coupled expression of p21, p27 or p53175P expression. The tetracycline-induced resumption of the cell cycle was also apparent by FACS analysis, since the respective populations adopted a FACS pattern identical to the control analysis of cells expressing pMF102.

7.2.4 Enhanced Productivity of Gytostatic, G1 Arrested CHO Cells

Although GFP is an excellent fluorescent marker protein for FACS analysis, it is not ideal to assess the industrial potential of CHO cells arrested in G1-phase of the cell cycle. In order to make an assessment of the ability of cytostatic cultures to synthesize and secrete heterologous proteins, the secreted alkaline phosphatase (SEAP), a well established reporter protein, was expressed in G1-arrested, cytostatic CHO cells. In contrast to GFP which is localized intracellularly, SEAP is secreted into the medium and is therefore closer related to the most industrially relevant products.

The dicistronic constructs pMF112, pMF113 and pMF114 (FIGS. 1 and 2), containing the SEAP gene transcriptionally linked to p21, p27 and p53175P, respectively, as well as the isogenic, monocistronic seap expression vector pMF111 as a control, were cotransfected into XMK1–9 concomitant with pMF102 at a ratio of 1:10 (GFP/SEAP constructs). The expression of GFP from pMF102 allowed FACS-mediated selection of transfected subpopulations as mentioned above, and the high ratio between pMF102 and the dicistronic expression vectors provides very high probability that every green fluorescent cell was also transfected by a dicistronic construct. 30'000 to 50'000 cells in G1-phase ranging from 103 to 104 in their green fluorescence intensity were sorted by FACS and subsequently cultivated for another 48 hours. All selected subpopulations showed the same mean green fluorescence, indicating approximately the same total content of SEAP expressing vector. The expression of the three cytostatic genes was routinely confirmed in the FACS-sorted, GFP expressing cells by immunofluorescence (data not shown). These cells showed the same behavior with respect to growth arrest as the ones transfected with pMF105, pMF106, pMF109. The SEAP activity determined in the culture supernatants of FACS-selected XMK1–9 populations harboring pMF112, pMF113 and pMF114 showed about 4 times higher SEAP production on average compared with the control population harbouring pMF111 (Table 3).

TABLE 2

SEAP productivity of CHO cell populations arrested in G1-phase. Productivity data listed are rates of SEAP activity accumulation in the medium of cultured cell populations containing approximately equal numbers of SEAP expression vectors. All data are normalized by the value for the population containing the pMF111 vector.

| Transfected vector | Genetic determinants | SEAP production |
| --- | --- | --- |
| pMF111 | SEAP | 1.00 ± 0.3 |
| pMF112 | SEAP, p21 | 4.62 ± 2.2 |
| pMF113 | SEAP, p27 | 3.90 ± 2.1 |
| pMF114 | SEAP, p53175P | 3.87 ± 0.8 |

The identical treatment of all transfected cells and subpopulations before and after FACS-mediated selection provides selected subpopulations harboring approximately same overall number of dicistronic expression vectors encoding SEAP as well as the cytostatic genes. This experimental setup allows direct correlation of the overall SEAP productivity between arrested and proliferating control cell populations as the total cell content SEAP encoding genetic elements in the population remain constant both the cytostatic and the proliferating control population.

Higher productivity of G1-phase arrested cell populations seems to be a general and intrinsic feature of this novel production process since all cytostatic genes used, although they act in different ways or have different molecular targets, show a similar, 4-fold overproduction of the model secreted product protein SEAP.

7.3 Discussion

By the conditional overexpression of the proliferation control genes p21, p27, and p53175P, we have reprogrammed one of the most widely used production cell lines, CHO, so that a critical part of the overall cell culture process, the production phase, reverts to the natural, cytostatic situation of protein synthesis and secretion. This novel bioprocessing concept can likely be adapted to other production cell lines since the genetic elements used (p21, p27 and p53) are common components of the cell-cycle regulatory system in different types of eukaryotic cells.

Normally, p53 overexpression is induced in cells subjected to genotoxic stress. The subsequent cell-cycle arrest in G1 allows the cells to repair defects and restore an optimal physiological state prior to cell division (Kastan et al., 1991, supra; Barak et al., 1993, supra; El-Deiry et al., 1994, supra). We chose to arrest cell proliferation at the G1 restriction point since it represents the natural checkpoint where cells replenish short-comings in physiological precursors and repair genetic defects which had accumulated during the previous cell cycle. We expect a cytostatic production phase at G1 checkpoint of the cell cycle to have a positive effect on the genetic stability of the production cell line as well as on the overall productivity of the production process as a functional protein production machinery is a prerequisite for this intrinsic and natural retrieval program. Furthermore, it has been recently reported that the rate of accumulation of total protein increases continuously during G1 (Kromenaker and Srienc, 1991, Biotechnol. Bioeng. 38:665–677).

Since p53 is implicated also in programmed cell death or apoptosis, we took advantage of the recently isolated p53 mutant, p53175P which showed a specific loss of apoptotic but not cell-cycle arrest function (Rowan et al., 1996, supra), to seek to minimize apoptotic response. The data do not indicate any sign of apoptosis due to the overexpression of these tumor suppressor genes. Single G1-arrested cells could re-enter the cell cycle after expression of these genes was reduced by addition of tetracycline to the culture medium. The cellular morphologies of the arrested cells also remained relatively normal, in contrast to morphologies observed following long-term arrest in response to DNA damage (Linke et al., 1996, supra).

In contrast to overexpression of p53, overexpression of p21 or p27 has to our knowledge never been reported to be linked to apoptosis. In fact, a recent report suggests p21, which is a primary component of p53-mediated cell-cycle arrest, counteracts activities which favor apoptosis (Polyak et al., 1996, supra). p21 may therefore protect cells from apoptotic response.

The goal of this experiment was to demonstrate proliferation arrest without undue metabolic disruption or stress response. Loss of cellular activity following blocking the cell cycle was a major concern prior to these experiments. However, the desired outcome is evident. Metabolism in these cytostatic cultures remains active, producing and secreting significantly increased amounts of heterologous protein, and avoiding necrosis. Apoptosis does not occur. Thus, these transient transfections studies have shown that many aspects of an ideal cytostatic process have been achieved, on the process time scale which can be examined in such experiments.

8. EXAMPLE

Cell Growth Arrest and Increased Production of Heterologous Gene Product in Cells Stably Transfected With Dicistronic Vectors That Coexpress a Heterologous Gene Product and a Tumor Suppressor Gene

8.1 Materials and Methods

Cell culture, transfection, immunofluorescence, flow cytometric analysis, SEAP assay and plasmid constructions were as described above in Section 7.

8.1.1 Selection Procedure for Stable Cell Lines

The cell line XMK1-9 was cotransfected with the plasmid of interest and the puromycin resistance conferring plasmid pPur (Clonetech) as described above. Transfected subpopulations were grown in the presence of selective FMX8 medium that also contained neomycin (400 µg/ml), to maintain constitutive expression of tTA, puromycin (6 µg/ml), to select for the integration of the plasmid of interest and 5 µg/ml tetracycline to silence the expression of the cytostatic gene contained on the multicistronic expression vector in order to alleviate counterselection of the desired stable clones. Selection medium was renewed every other day to maintain high selective pressure and to compensate for the breakdown of tetracycline. The maintenance of absolute repression of the multicistronic expression unit during this selection procedure is a prerequisite for the production of stable clones as even low expression of the cytostatic genes could result in proliferation arrest of respective transfected cells and their subsequent loss as a consequence of the growth disadvantage. Sporadic SEAP activity assays during the selection procedure which were negative guaranteed that the multicistronic expression units are tightly repressed and that no clones began to grow which avoided the strict tetracycline-mediated control of SEAP expression, e.g. by genetic rearrangements leading to the disruption of the gene linkage in the multicistronic expression unit.

The mixed population was harvested after approximately 8 days and subjected to dilution cloning. During dilution cloning the same selection procedure was applied as described above. The clones emerging from this dilution cloning were tested for regulated expression of all genes contained in the multicistronic expression unit either by using immunofluorescence microscopy, Western blot analysis or the SEAP activity test. Regulated clones were subjected to a further round of cloning before pure clones were considered for further experiments.

8.1.2 Determination of the Growth Behavior of Stable Cell Lines

The growth behavior of stable cell lines was determined over a period of five days in the absence of tetracycline in the culture medium and compared to the proliferation-competent control cell line 111-10. Into each of 5 identical cell culture flasks (T25) an initial cell population of $2 \times 10^5$ cells was seeded. Every day, the cells of one flask were completely detached with dissolvation solution (Sigma), resuspended in filter-purified Casyton buffer (pH 7.3; 7.93 g/l Nacl; 0.38 g/l $Na_2EDTA$; 0.4 g/l KCl; 0.19 g/l $NaHPO_4$; 1.95 g/l $Na_2H_2(PO4)_2$; 0.3 g/l NaF) according to the manufacturer's protocol and the cell number was determined as the average of 6 independent readings taken by a Casy®1 cell counter (Schärfe System). Concomitantly with the daily determination of the total cell number the SEAP productivity was measured over a period of five days (see above).

8.2 Results 8.2.1 Construction of Stable Cell Lines Expressing the Model Product Gene SEAP and the Tumor Suppressor Genes from a Single Dicistronic Expression Unit The vectors pMF112 (SEAP-p21), pMF113 (SEAP-p27), and pMF114 (SEAP-p53175P) as well as the isogenic, monocistronic control vector pMF111 (SEAP only) were transfected into the CHO-K1 derivative XMK1-9 which constitutively expresses the tetracycline-responsive transactivator. The whole selection procedure for the generation of stable clones harboring the dicistronic or the control expression vectors was carried out in the presence of tetracycline to suppress the expression of the tumor suppressor genes and to alleviate consequential counterselection of the desired clones due to the growth disadvantage resulting from the expression of the cytostatic gene.

Individual resistant clones emerging upon selection on the antibiotic resistance marker (puromycin) cotransfected were grown in the absence of tetracycline to assess their production of the model product protein SEAP. The expression of the respective tumor suppressor genes encoded by the second cistron was shown by immunofluorescence. Clones which showed adjustable regulation of both genes were recloned using the limited dilution method and were tested a second time prior to further analysis.

The only construct which resulted in stable clones was, besides the control plasmid pMF111, the p27-expression vector pMF113. Nevertheless, two cell lines were found which stably contain the SEAP-p53175P expressing construct, both of which showed, however, a particular cell morphology upon induction of the dicistronic expression unit which is highly suggestive of apoptosis and died subsequently. Perhaps a stable, ongoing expression of p53, even in this mutated form which is not supposed to cause apoptosis, is enough to cause problems in this configuration. Stable cell lines harboring pMF112 could not be generated at all. Both observations show that potential problems of cytostatic cell culture processes reside either in deleterious effects of the tumor suppressor gene on the host cell when overexpressed or induced (p53175P) or might originate from residual cytostatic activity emanating from the leakiness of the tetracycline-regulatable promoter and consequential counterselection of these cells during the selection process.

8.2.2 Proliferation Potential of CHO Cell Lines Stably Expressing p27 from the Dicistronic Expression Unit Whereas the growth behavior of the control cell line 111-10 (harboring pMF111) remains identical irrespective of the presence or the absence of tetracycline in the culture medium the SEAP-p27 producing cell lines (113-6B, 113-10B, 113-30B, and 113-31B), while showing a growth rate similar to the control cell line in the presence of tetracycline, became growth arrested in the absence of tetracycline since the dicistronic expression unit was induced. Cell lines expressing p27 show an immediate and sustained growth arrest in the G1 phase over the five days period and no particular morphological changes highly suggestive for apoptosis as seen with p53 overexpressing cells could be observed. However, these proliferation-inhibited, surface-attached cells display a higher overall cell surface probably as a result of reaching out to form cell-to-cell contacts. Arrested cells remain proliferation-inhibited over extended periods (up to or >two weeks) and probably beyond this time. However, after two weeks of continuous culture, growth-inhibited cells are counterselected by mutated variants which alleviated the engineered growth-inhibitory signals most often by deleting or mutating the dicistronic expression unit.

8.2.3 Productivity of Proliferation-inhibited, p27 Expressing Cell Lines

As the model product gene seap is concomitantly expressed from the same dicistronic expression unit as the tumor suppressor gene p27, the productivity of the growth-inhibited cells could be directly assessed in an isogenic background and compared to the control cell line 111-10. The control cell line 111-10 represents the highest SEAP-producing stable clone that could be generated by the transfection of XMK1–9 with pMF111. The SEAP productivity (SEAP activity/cell number) of both the growth-arrested (P) and the proliferation-competent control cell lines (P*) were separately measured under tetracycline-free conditions and plotted as the relative productivity (P/P*) of the proliferation-inhibited cell line compared to the control cell line 111-10. Thus, the factor P/P* is a quantitative measure indicating the n-fold higher productivity of growth-arrested cells (FIG. 3). The production potential of a secreted, heterologous protein, represented by the model product protein SEAP, by proliferation-inhibited cells was about 10 times higher on average when compared to proliferation-competent control cells (FIG. 3). The extent of the increase in productivity always correlates with the strength and the sustenance of the growth arrest during the five days period (see below). Correspondingly, the cell lines 113-10B and 113-30B which show a less restricted growth behavior in tetracycline-free culture medium produce approximately 30% less SEAP than the virtually completely proliferation-inhibited cell lines 113-6B and 113-31B. The average productivity of stable, growth-arrested cell lines even exceeds the overall productivity of FACS-selected, transiently transfected pMF113-containing CHO subpopulations (described above in Section 7).

8.3 Discussion

The results demonstrate that CHO stably transfected with a SEAP-p27 expression construct showed, upon induction, the same growth arrest as transiently transformed cells. The stable cell lines also resumed growth upon repression of the p27 gene, even following prolonged periods of growth inhibition. This suggests that p27-induced proliferation-inhibition does not reduce cell viability or induce programmed cell death. Additionally, production of SEAP from the stably transformed SEAP-p27 containing cells showed a 5-fold increase over that seen in transient experiments (up to a total of 15-fold increase in production as compared to the SEAP control construct).

Only two cell lines were found which stably contain the SEAP-p53175P expressing construct. When these cells are switched to medium in which expression of p53 is activated, we see unusual cell morphology which is highly suggestive of apoptosis. Furthermore, unlike with growth-arrested cell lines expressing p27, the cell-cycle block using p53 is not reversible and cells die shortly after induction. Perhaps ongoing expression of p53, even in this mutated form which is not supposed to cause apoptosis, is enough to cause problems in this configuration. The ability of p53 to induce apoptosis is now generally accepted; however, its extent varies in different cell lines.

Stable cell lines harboring pMF112 could not be generated at all. In the natural cellular situation, p21 inhibits DNA replication and enhances DNA repair by interaction with the replication and repair factor, the proliferating cell nuclear antigen designated PCNA. Only at high concentrations does p21 also inhibit the function of cyclin-dependent kinases (Cdks), particularly those that function during the G1-phase of the cell cycle. Thus, it may be that sufficient levels of p21 were not achieved in the stably transfected constructs.

9. EXAMPLE

Construction of the Tricistronic pTRIDENT Family of Vectors 9.1 Materials and Methods Cell culture, transfection, immunofluorescence, flow cytometric analysis and SEAP assay were as described above in Sections 7 and 8.

9.1.1 Construction of the pTRIDENT Cloning Vectors

In order to expand existing dicistronic vector systems which allow the cap-independent, IRES-mediated transcription of the second cistron to the tricistronic level, we constructed plasmids containing IRES and IRES-EV cassettes flanked by multiple restriction sites.

IRES II was amplified by PCR from pSBC-1 (Dirks et al., 1993, supra) with oligos OMF40:

GATCGAATTCGCGGCCGCGGCCGGC-CCGGGCGCGCCTGATCAATCGATGTT-TAAACttaaa acagctctggggt (SEQ ID NO:7), and OMF41:

GATCAGATCTGTTTAAACGCGTATT-TAAATTAATTAAGCGATCGCAC-TAGTCTCGAGaatc caattcgctttatg (SEQ ID NO:8).

The restriction sites contained in the extension (capital letters) of the 5' oligo (OMF40: EcoRI, NotI, FseI, NaeI, SrfI, AscI, BssHII, BclI, ClaI, PmeI) represent MCSII (NotI to PmeI) except EcoRI which was included for convenient cloning into pSG5. Likewise, the extension (capital letters) of the 3' oligo (OMF41: XhoI, SpeI, SgfI, PacI, SwaI, MluI, PmeI, BglII) represent MCSIII (XhoI to BglII) of the pTRIDENT vector system (FIG. 4). The resulting PCR fragments were ligated via EcoRI/BglII to the corresponding sites of the multiple cloning site (MCS) of pSG5 (Stratagene, #216201) to give plasmid pMF117.

In addition to IRES, we used another picornaviral element, the cap-independent translation enhancer element from encephalomyocarditis virus (IRES-EV) to initiate translation of the third cistron.

The IRES-EV cassette was constructed by amplifying the CITE element from pCITE-4c(+) (Novagen, Madison, Wis., #69915-1) with oligos OMF42:

GATCGAATTCGCGGCCGCGGCCGGC-CCGGGCGCGCCTGATCAATCGATGTT-TAAACgttat tttccaccatattg (SEQ ID NO:9) and OMF43:

GATCAGATCTGTTTAAACGCGTATT-TAAATTAATTAAGCGATCGCAC-TAGTCTCGAGaatc gtgttttcaaagg (SEQ ID NO:10). As IRES-EV should be flanked by the same MCSII and MCSIII sites as the IRES cassette, OMF42 and OMF43 contain identical restriction sites in their extensions (capital letters) as the ones used for the amplification of IRES. Correspondingly, the IRES-EV cassette was cloned EcoRI/BglII into the same sites of pSG5 to give pMF118. The amplified IRES-EV sequence corresponds to bp 335–826 of Duke et al. (1992), J. Virol 66:1602–1609.

The major reason to consider a IRES-EV element for the translation of the third cistron instead of second IRES identical to the first one was the concern that such duplicated sequence elements might lower the genetic stability of the whole construct. Both elements, IRES and IRES-EV, lack significant DNA homology, yet the secondary structure of their transcripts is highly conserved (Belsham and Sonenberg, 1996, Microbiological Reviews 60:449–511).

Previous studies have shown that the sequence context around the authentic initiator codon, the 11th AUG of the 5' ntr of the EMC virus, may dramatically influence in vitro translation (Jackson et al., 1990, TIBS 15:477–483; Kaufman et al., 1991, Nucleic Acids Res. 19:4485–4490; Davies and Kaufman, 1992, J. Virol. 66:1924–1932; Rees et al., 1996, BioTechniques 20, 48–56). We therefore mutated AUG 10 to alleviate an out of frame translation start (Kaminski et al., 1990, EMBO J. 9:3753–3759) and deleted the major initiation codon AUG 11, the role of which is taken over by the AUG of the gene of interest cloned into MCS III.

pSG5 was used as the cloning vector for the IRES and IRES-EV cassettes since it places the picornaviral element upstream of a SV40 polyadenylation site (pA) followed by the bacterial origin of replication (ori) of the high copy number pBluescript® vector (Stratagene) and the ampicillin resistance gene (bla) (FIG. 4). The NotI/SspI fragments of pMF117 and pMF118 containing MCSII-IRES II or IRES-EV-MCSIII-SV40 pA—pBluescript® ori-bla were fused to the SspI/NotI fragments of pTBC1 (Dirks et al., 1994, supra) containing the tetracycline-inducible promoter PhCMV*-1, MCSI (EcoRI, XbaI, SalI, PstI, HindIII) and the first IRES element. pTRIDENT1 is the result of the above mentioned fusion of pTBC1 and pMF117 and pTRIDENT3 is the result of the fusion between pTBC1 and pMF118.

Besides pTRIDENT1 and pTRIDENT3 which allow adjustable, simultaneous expression of all three cistrons by tetracycline, the transcription of the tricistronic expression vectors pTRIDENT2 and pTRIDENT4 which resulted from the NotI/SspI fusion of pMF117 and pMF118 with PSBC1 (Dirks et al., 1993, supra), is driven by the constitutive SV40 promoter.

Another set of pTRIDENT vectors contains the recently reported ecdysone-regulatable promoter which allows adjustable gene expression in response to this insect hormone and its derivatives (No et al., 1996, et al.; Invitrogen). The promoter-containing region of pTRIDENT1 and pTRIDENT3 (SspI/EcoRI) was replaced by the SspI/EcoRI fragment of pIND (Table 1; Invitrogen) containing the ecdysone-responsive promoter (PEC) to give plasmids pTRIDENT7 and pTRIDENT8, respectively.

Figure 4A:
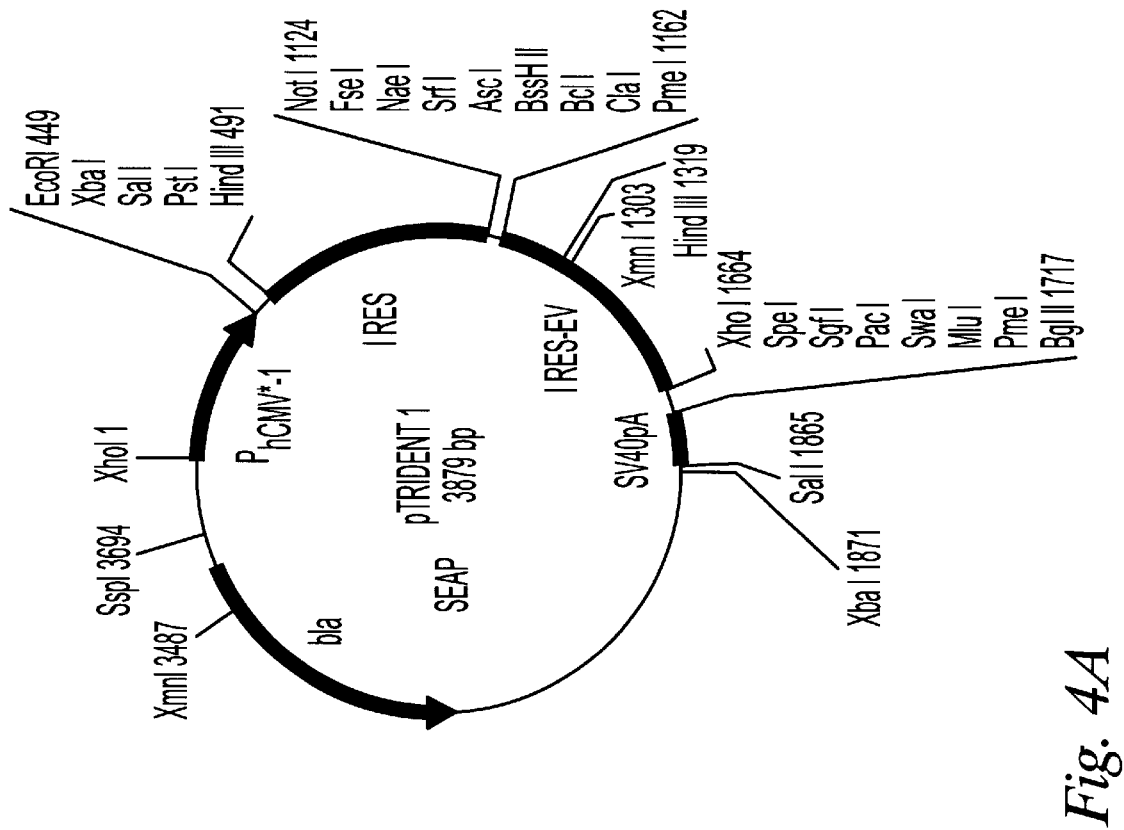
Figure 4A:
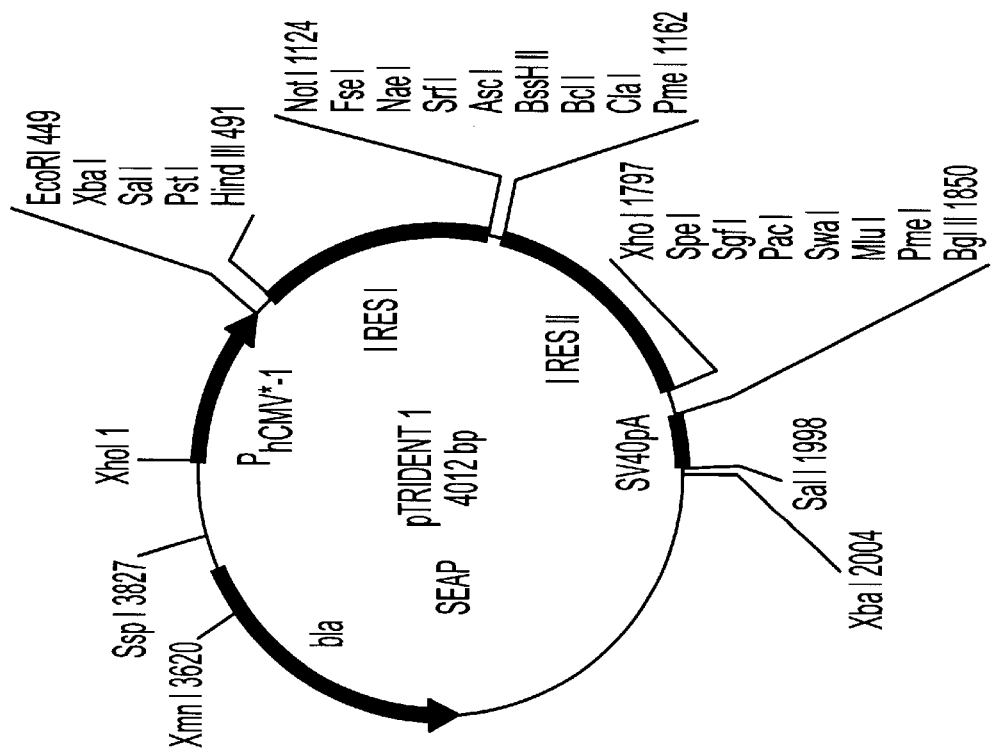
Figure 4B:
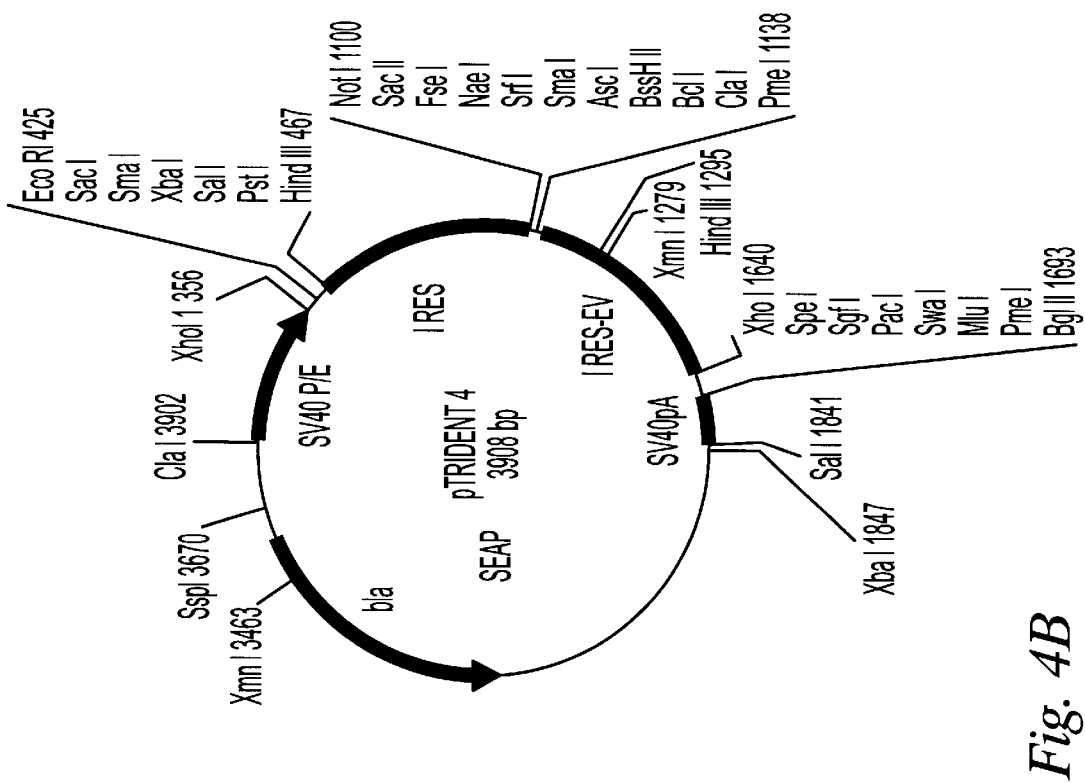
Figure 4B:
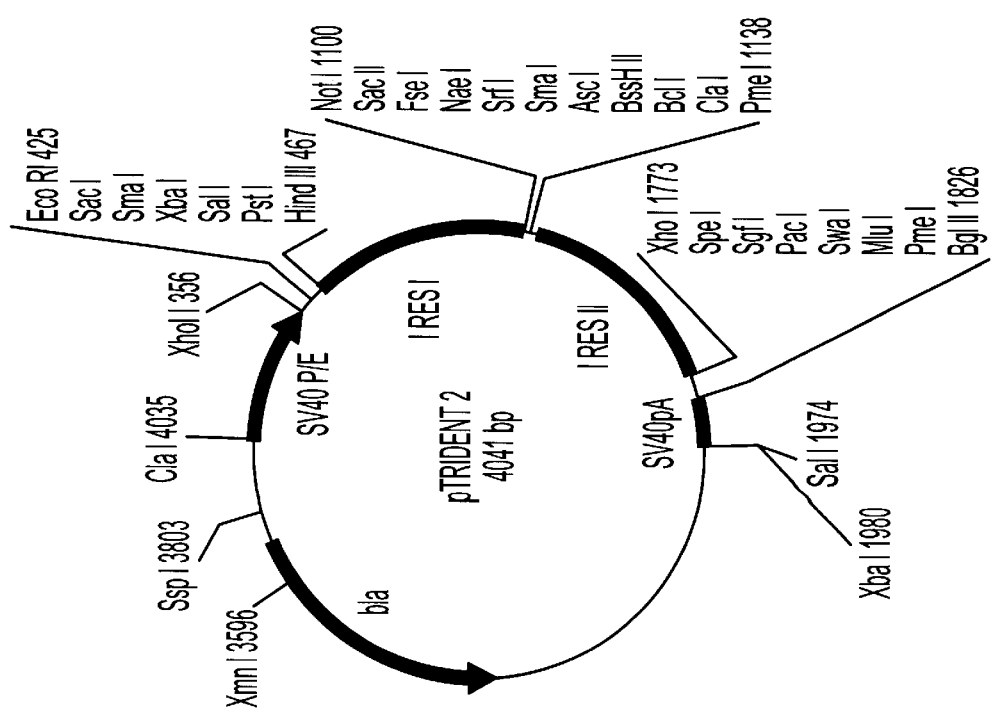
Figure 4C:
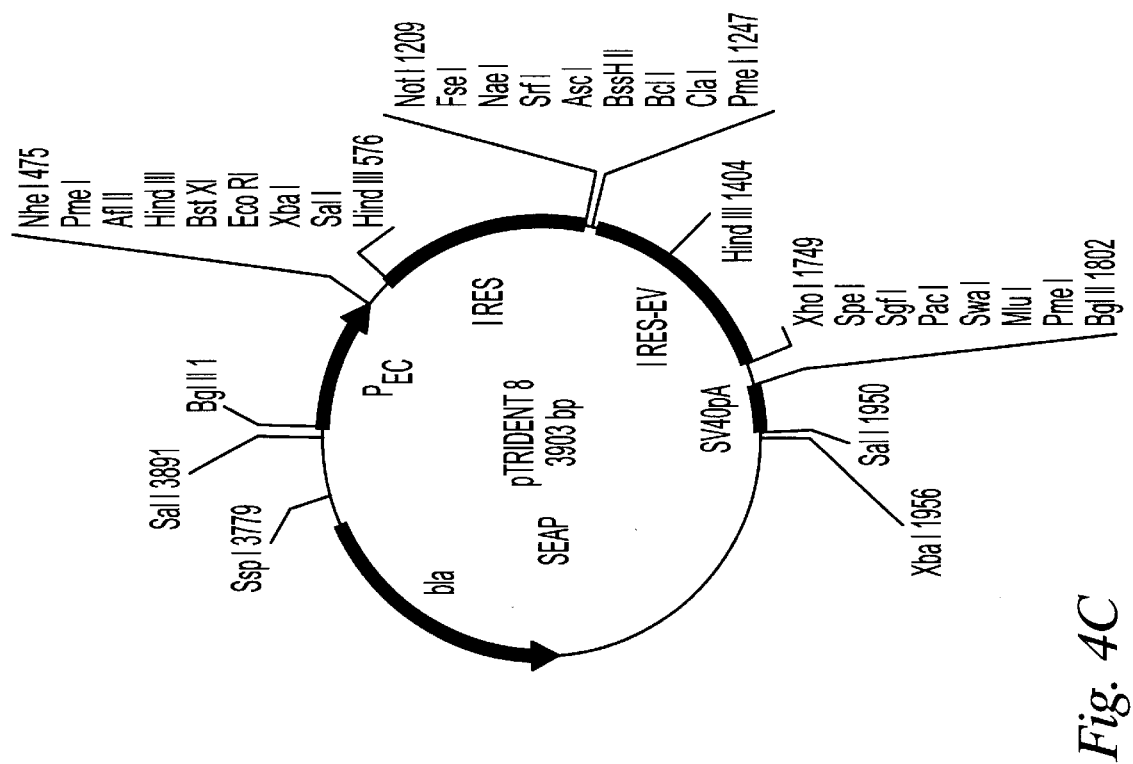
Figure 4C:
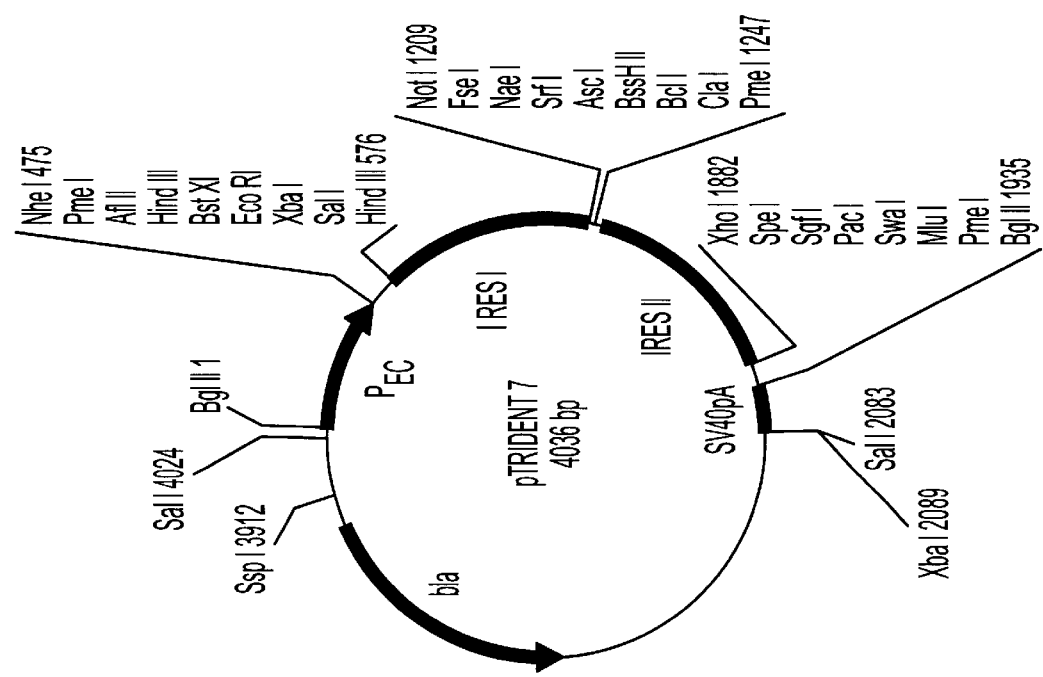

9.1.2 Construction of the pTRIDENT Derivatives pTRIDENT derivatives are all based on pTRIDENT1 and pTRIDENT3 (FIG. 4; see above) containing both the tetracycline inducible promoter PhCMV*-1 (Gossen and Bujard, 1992, et al.) and either a second IRES (pTRIDENT1; IRES II) or a IRES-EV element (pTRIDENT3) for the translation of the third cistron (FIG. 4A).

SEAP, the product reporter gene encoding the human secreted alkaline phosphatase was cloned via an EcoRI/HindIII fragment from pSBC2-SEAP (Dirks et al., 1993, supra) into the corresponding sites of pTRIDENT1 and pTRIDENT2 to give plasmids pMF124 and pMF127, respectively. In order to achieve expression of p21 from the second cistron, a p21 containing cDNA fragment was amplified from plasmid pBSSK-/p21 (El-Deiry et al., 1993, supra) with primers OMF44:

GATCACTAGTGATATCGCGGCCGCT-TCGCCGAGGCACCGAGG (SEQ ID NO: 11) and OMF45:

GATCATCGATGGATCCGCCCGGGCT-TAGGGCTTCCTCTTGGAG (SEQ ID NO: 12). The resulting PCR product was cloned via the NotI/BamHI sites contained in the oligos into the NotI/BclI sites of pMF124 and pMF127 to produce pMF130 and pMF129, respectively.

The GFP cycle 3 mutant of the green fluorescent protein (GFP) was used to monitor overall protein production originating from the transcription and translation of the third cistron (Affimax Research Institute, Palo Alto, Calif.; Crameri et al., 1996, Nature Biotechnolgy 14, 315–319). GFP cycle 3 mutant was amplified from Alpha+GFP using primers OMF52:

GATCACTAGTGCGATCGCTTAATTAA-GATCCAAGCTGCCTCGAG (SEQ ID NO: 13) and OMF53: GATCAGATCTACGCGTATTTAAATT-TACTTGTACAGCTCGTCC (SEQ ID NO: 14) and cloned blunt ended into pCR-Script amp SK(+) (Stratagene #211190) to give pMF131. Similarly, GFP cycle 3 mutant was amplified from Alpha+GFP using primers OMF34: GATCGAATTCGATCCAAGCT-TGCCTCGAG (SEQ ID NO: 15) and OMF37: GATC-CTGCAGCCCGGGTTATTTGTAGAGCTCATC (SEQ ID NO: 16) and ligated via EcoRI/PstI into pTBC1 to give the monocistronic control plasmid pMF104. Subsequently, GFP was excised from pMF131 by SpeI/BglII and ligated to the corresponding sites of pMF129 and pMF130 to give pMF132 and pMF133, respectively.

9.2 Results pMF132 and pMF133 contain tricistronic expression units which encode seap, p21 and GFP in a row and form, together with the tetracycline inducible promoter PhCMV*-1, an artificial "eukaryotic operon". Whereas the translation of the first cistron (seap) is based on classical, cap-dependent translation-initiation, the second one (p21) relies on cap-independent, IRES-mediated translation and the third cistron is translated either by a second IRES, IRES II (pMF132: PhCMV*-1-seap-IRES I-p21-IRES II-GFP), or IRES-EV element (pMF133: PhCMV*-1-seap-IRES-p21-IRES-EV-GFP). pDD5 (PhCMV*-1-seap-IRES I-p21-IRES II-bcl-2) and pDD1 (PhCMV*-1-seap-IRES-p21-IRES-EV-bcl-2) and are equivalent to pMF132 and pMF133 except that GFP has been replaced by bcl-2.

We transfected the CHO cell line XMK1–9 with the tricistronic expression vectors pMF132 and pMF133 and investigated the simultaneous, as well as the adjustable, expression of all three genes. Table 2 shows SEAP production of the tricistronic expression vectors pMF132 and pMF133.

TABLE 2

SEAP and GFP production of mono- and tricistronic expression vectors

| Plasmid | DNA construct | SEAP | GFP |
|---|---|---|---|
| pMF111 | PhCMV*-1 - SEAP | 1.00 ± 0.3 | — |
| PMF104 | PhCMV*-1 - GFP | — | 1.00 ± 0.07 |
| pMF132 | PhCMV*-1 - SEAP - IRESI - p21 - IRESII - GFP | 0.87 ± 0.9 | 0.48 ± 0.13 |
| pMF133 | PhCMV*-1 - SEAP - IRESI - p21 - IRES-EV - GFP | 0.92 ± 1.1 | 0.64 ± 0.09 |

Given the identical position to the promoter PhCMV*-1 and its cap-dependent translation, SEAP production from plasmids pMF132 and pMF133 was expected to be as high as the production from the isogenic, monocistronic expression vector pMF111 (above). As shown in Table 2 there is no significant difference in SEAP production from the monocistronic construct compared to the tricistronic one. This result implies that the tricistronic mRNA transcribed from the tricistronic expression unit remains relatively stable inside the cell.

The expression of the second cistron containing the cyclin kinase inhibitor p21 was monitored by immunofluorescence. The expression from both plasmids was several-fold higher than the intrinsic background production of p21 in CHO cells and equals the production level from the isogenic, dicistronic control plasmid pMF112. Similarly, overexpression of bcl-2 in the third cistron was several fold higher than the background production of XMK1–9 cells and, as judged from immunofluorescence data, there were no detectable differences in the expression levels of bcl-2 translated from IRES II (pDD5) or IRES-EV (pDD1).

In the same way, there were no perceptible differences in the IRES II-(pMF132) and IRES-EV-(pMF133) mediated translation of the third cistron as judged from the green fluorescence produced by transfected cells XMK1–9. Visual comparison of the green fluorescence produced from the third cistron with the one produced by cap-dependent translation of the isogenic, monocistronic, control vector pMF104 revealed no significant difference. However, quantitative fluorescence data derived from FACS analysis show approximately 2-fold lower green fluorescence when GFP is expressed from the third cistron compared to its expression from the first one (Table 3).

Probably owing to the deletion of AUG 10, one of its potential translational start codons, the IRES-EV element enhances cap-independent translation in the same order of magnitude as the IRES element, which has previously been reported to be about 10-fold more efficient than the IRES-EV element (Kaufman et al., 1991, supra; Dirks et al., 1993, supra).

9.3 Discussion

The modular construction of the pTRIDENT vector system has several advantages over dicistronic expression vectors available and is flexible enough to cope with future applications:

(1) The pTRIDENT-based tricistronic expression plasmid is a one-vector system which allows the consecutive cloning of three individual genes. Seven different sites for restriction endonucleases recognizing 8 bp in MCS II and MCS III alleviate conflicting cloning situations due to sites already contained within the open reading frame of genes ligated into the vector system in previous steps. Earlier versions of dicistronic expression vectors either contain already a fixed genetic marker (Kaufman et al., 1991, supra; Kim et al., 1992, Mol. Cell. Biol. 12:3636–3643; Sugimoto et al., 1994, Bio.Technology 12:694–698; Rees et al., 1996, supra) or had to be fused from independently constructed monocistronic expression vectors (Dirks et al., 1993 and 1994, supra). Such a fusion of monocistronic expression vectors to generate the dicistronic expression unit is not only cumbersome but also limited by the availability of restriction sites for this process; e.g., fusion of the monocistronic expression vectors by Dirks et al. (1993), supra, can only be achieved if none of the two genes contain a NotI site and if one of the 6 bp cutting restriction enzymes VspI, SspI or XmnI is still available for the fusion step.

(2) The pTRIDENT system is fully compatible via its XmnI/NotI or SspI/NotI sites with the multifunctional vector family by Dirks et al. (1994), supra, which offers a collection of promoter and vector backbones useful for a wide variety of applications. Furthermore, the pTRIDENT system is compatible with the monocistronic expression vectors and the dicistronic vector system of Dirks et al. (1993), supra, via the same sites.

(3) Useful promoter-IRES I-IRES II/IRES-EV, IRES I-IRES II/IRES-EV-pA, as well as individual IRES or IRES-EV containing cassettes can be generated from the pTRIDENT vectors using the XhoI, SalI or other restriction sites contained in one of the three MCS, respectively.

(4) Transfer of genes among existing pTRIDENT vectors already expressing three independent cistrons is facilitated at all positions using either exclusively the remaining restriction sites contained in the MCS, among them at least one 8 bp blunt end cutting and one BamHI-compatible site, or in conjunction with the XmnI or SspI sites in the vector backbone, respectively. The third cistron, possibly containing a marker gene, is most easily exchanged via the PmeI sites. The same sites can be used to eliminate the third cistron from the pTRIDENT vector to generate a dicistronic derivative. Similarly, the BclI site in MCS I and the BglII site in MCS III could be used for the elimination of the third cistron as could the SmaI sites in MCSI and MCSII of pTRIDENT2 and pTRIDENT4 for the deletion of the first cistron.

By the expression of three independent genes from a single tricistronic expression unit contained in the pTRIDENT vectors we demonstrated the successful expansion of the concept of multicistronic, eukaryotic gene expression to the tricistronic level. No significant differences in cistron I- and cistron II-based protein production levels, when compared to the expression levels of the corresponding cistrons of dicistronic, expression vectors (Dirks et al., 1993, supra; Macejak and Sarnow, 1991, Nature 353:90–95), were found. Even the genes encoded by the third cistron were highly expressed and showed only an overall 2-fold lower expression level when compared to cap-dependent translation irrespective of whether the cap-independent translation was based on the IRES or IRES-EV elements.

The translation efficiency of IRES-EV has previously been shown to be dependent on the sequence context surrounding the initiation codon AUG11 (Kaufman et al., 1991, supra). The deletion of the out-of-frame AUG10 codon in the IRES-EV elements used in the pTRIDENT vectors may reduce erroneous translation initiation from AUG10 and may increase the overall translation efficiency (Kaufman et al., 1991, supra; Duke et al., 1993). Our expression data, above all the ones from the third cistron, support earlier findings by Kaufman et al. (1991), supra, Dirks et al. (1993), supra, and Rees et al. (1996), supra, describing a general tendency of lower cap-independent translation efficiency compared with cap-dependent translation. Such a relative lower translation efficiency of the third cistron could be advantageous when expressing gene products deleterious to the cells or gene products, such as those involved in engineering of metabolism, which are not desired at high levels. Furthermore, in dicistronic systems, a low, IRES-EV-mediated translation efficiency of resistance genes such as dihydrofolate reductase (DHFR, methotrexate resistance) or the neomycin phosphotransferase (NPT II, neomycin resistance) has been shown to be compensated in stable clones by the selection of chromosomal integration sites with high gene expression (Kaufman et al., 1991, supra; Rees et al., 1996, supra).

We expect the pTRIDENT family of expression vectors to be a useful tool which could significantly contribute to and speed up research focusing on combinatorial effects of different genes and/or multifaceted processes in mammalian cells. Furthermore, tricistronic expression allows a "three-in-one" step metabolic engineering of animal cells without the need for subsequent rounds of transfection and selection. Multiple rounds of transfection and selection increase not only the risk of undesired position effects by constructs stably integrated into the chromosome and but also imply the maintenance of selective pressure with several compounds which may lower the cost-efficiency of large scale applications.

Although we expected stability problems using the two genetic elements IRES I and IRES II on the same vector as in pTRIDENT1, pTRIDENT2, pMF132 and pDD5, no genetic rearrangements could be observed in E. coli. Given a strictly correlated expression of genes contained in the tricistronic expression vector and given the fact that the frequency of homologous recombination is several orders of magnitude lower in eukaryotic cells, we do not consider the use of pTRIDENT1 and pTRIDENT2 derivatives problematic with regard to genetic stability. However, in technologies such as the production of transgenic animals and specialized applications such as gene therapy which rely on homologous recombination, the use of pTRIDENT3 and pTRIDENT4 derivatives could be advantageous since they do not contain duplicated genetic elements.

10. EXAMPLE

Coexpression of a Tumor Suppressor Gene and a Survival or Antiapoptosis Gene Further Increases Production of Heterologous Gene Product

10.1 Materials and Methods

Cell culture, transfection, immunofluorescence, flow cytometric analysis, SEAP assay, plasmid constructions and selection for stable transfectants were as described above in Sections 7 and 8. Additional antibodies specific for Bcl-2 (rabbit polyclonal (Æ21) cat# sc-783, lot# A137; mouse monoclonal Bcl-2 (100), cat# sc-509, lot# C187), Bcl-$x_{S/L}$ (rabbit polyclonal (S-18), cat# sc-634, lot# L106), and C/EBPα (rabbit polyclonal (14AA), cat# sc-061, lot# L046) were purchased from Santa Cruz Biotechnology Inc.

10.1.1 Western Blot Analysis

The cell lines DD6-X1 and DD6-X2, which were both transfected with the pTRIDENT derivative pDD6 (see below) and thus allow the conditional and co-ordinated expression of SEAP-p27-bcl-$x_L$, were examined by Western Blot analysis to confirm regulated expression of Bcl-$x_L$. Western blot analysis of Bcl-x was necessary as the only commercially available anti-Bcl-x antibody (Santa Cruz Biotechnology Inc., rabbit polyclonal (S-18), cat# sc-634, lot# L106), crossreacts with both isoforms of the Bcl-x protein (the shorter, apoptosis-inducing form Bcl-$x_S$ and the alternatively spliced, longer form Bcl-$x_L$ which inhibits programmed cell death). $5 \times 10^5$ cells were grown both in the presence as well as the absence of tetracycline before cytoplasmic extracts were prepared. The cells were detached from the culture vessel, washed twice with PBS and resuspended in lysis buffer (1% IGEPAL (Sigma, CA-630), 150 mM NaCl, 50 mM Tris, pH 7.5, 1 mM EDTA, 1 mM PMSF, 21 µg/ml aprotinin, 10 µg/ml leupeptin) for 30 min. on ice (adapted from Behrens et al, 1994, J. Immunol. 153:682–690). Cells were then sonified twice for 1 min. on ice before the cell lysate was centrifuged at 14'000×g for 10 min. at 4° C. The protein concentration of the supernatant was determined using a BCA* protein assay (Pierce) according to the manufacturer's protocol. Equal protein concentrations were applied on a 12.5% polyacrylamide-SDS gel and the proteins were subsequently blotted onto nitrocellulose using a Bio-Rad electroblotter (Sambrook et al., 1989, supra). The blot was developed using the primary antibody against Bcl-$x_{S/L}$ described above and the ECL Western Blot kit (Amersham) using the manufacturer's suggested protocol.

10.1.2 Plasmid Constructions (FIG. 5)

In this experiment, we constructed additional tricistronic expression vectors which are isogenic to their dicistronic counterparts (described above in Section 6) for the expression of SEAP and p21 or p27 from the first and second cistron, respectively, but contain an additional third cistron which encodes either of the survival factors bcl-2 (Tsujimoto and Croce, 1986, Proc. Natl. Acad. Sci. USA 83:5214–5218), bcl-$x_L$ (Boise et al., 1993, supra) or the p21 stabilizing differentiation factor c/ebpα (Timchenko et al., 1996, supra). These tricistronic expression vectors are based on pTRIDENT1 and pTRIDENT4 (described above in Section 9). Both expression units are driven by PhCMV*-1 and contain either two identical picornaviral internal ribosomal entry site (IRES, pTRIDENT1) or an IRES element and a cap-independent translation enhancer (IRES-EV, specially mutated for increased translation efficiency) of the encephalomyocarditis virus (EMCV) to guarante cap-independent translation of the second and the third cistron, respectively.

SEAP was cloned into the first cistron of pTRIDENT1 and pTRIDENT4 by cutting the monocistronic, SEAP production vector pMF111 (described above in Section 7) with EcoRI/HindIII and ligating the SEAP gene to the corresponding sites of pTRIDENT1 and pTRIDENT4 to give pMF127 and pMF124, respectively. Subsequently, pMF124 was cut with NotI and BclI for subcloning in either a p21 or p27 coding region. p27 was amplified from plasmid pMF113 with the following primers:

OMF46; GATCACTAGTGATATCGCGGCCGCGCG-GTCGTGCAGACCCGG (SEQ ID NO:17) and

OMF47; GATCATCGATGGATCCGCCCGGGCT-TACGTTTGACGTCTTCTTCTG (SEQ ID NO:18).

p21 was amplified from plasmid pMF112 with primers OMF44 and OMF45 as described above.

Both the p27 and p21 fragments were cloned as NotI/BamHI fragments into the NotI/BclI sites of pMF124 to give plasmids pMF128 (p27) and pMF130 (p21), respectively. Similarly, pMF127 was cut with NotI/BclI and PCR-amplified p21 (OMF44 and OMF45) was cloned in as a NotI/BamHI fragment to give pMF129.

The coding regions for survival factors bcl-2 and bcl-$x_L$ were cut out of pSFFNeo-bcl2 (Tsujimoto and Croce, 1986, supra) and pSFFNeo-bclx$_L$ (Boise et al., 1993, supra) by EcoRI and cloned into pBluescript II SK⁻ placing these genes under the control of the lacZ promoter to give plasmids pMF137 (bcl-2) and pMF138 (bCl-x$_L$), respectively. Similarly, the human differentiation factor c/ebpα contained in pCMVα (Timchenko et al., 1996, supra) was restricted with BamHI and ligated to the corresponding BamHI site of pBluescriptII SK⁻ (pSS2), thus placing this differentiation factor under the control of the lacZ promoter. pMF137 and pMF138 were restricted with SpeI/EcoRV and the corresponding genes, bcl-2 and bcl-x$_L$ were either ligated to the SpeI/SwaI sites of pMF128 to give plasmids pDD4 (SEAP-p27-bcl-2) and pDD6 (SEAP-p27-bcl-x$_L$) or to pMF130 to give pDD1 (SEAP-p21-bcl-2) and pDD3 (SEAP-p21-bcl-x$_L$) (FIG. 5). In the same way, pSS2 was restricted by SpeI/EcoRV and ligated to pMF129 (SpeI/SwaI) to produce plasmid pSS5 (SEAP-p21-c/ebpα).

The expression of the genes encoded on these pTRIDENT derivatives was tested by immunofluorescence analysis or the SEAP activity test following transient transfection of the respective tricistronic expression vectors into XMK1–9 as described above.

10.2 Results 10.2.1 Additional Expression of Survival Genes Concomitant with SEAP and the Tumor Suppressor Genes p21 and p27 from a Tricistronic Expression Unit In order to further improve the cytostatic process, we made use of the tricistronic expression technology described above which allowed us to express survival genes such as bcl-2 and bcl-x$_L$ in addition to SEAP and the tumor suppressor genes in a co-ordinated fashion from the third cistron of a single, tricistronic expression unit. Tricistronic vectors which contain all combinations of tumor suppressor genes (p21 or p27) and survival genes (bcl-2 or bcl-x$_L$) pDD1 (SEAP-p21-bcl-2), pDD3 (SEAP-p21-bcl-x$_L$), pDD4 (SEAP-p27-bcl-2), and pDD6 (SEAP-p27-bcl-x$_L$) are, apart from the third cistron, isogenic to the dicistronic expression vectors described above (see Section 6).

As for the dicistronic expression vectors pMF112, pMF113, and pMF114, the tricistronic vectors pDD1, pDD3, pDD4, and pDD6 were transfected into XMK1–9. Unlike with the dicistronic, p21-encoding construct pMF112, two stable cell lines could be generated which harbor the tricistronic, p21-containing expression vector pDD1. Both cell lines showed high, as well as tetracycline-regulatable, expression of all three cistrons but displayed no proliferation arrest and consequently no productivity advantage over the control cell line 111-10 under conditions that allow full expression of the tricistronic expression unit (data not shown). Several attempts to generate stable clones by transfecting XMK1–9 with plasmids pDD3 and pDD4 did not succeed. However, the transfection of pDD6 the tricistronic expression unit of which consists of SEAP-p27-bcl-x$_L$ resulted in the generation of the stable cell lines DD6-X1, DD6-X2, and DD6-X3.

As for the cell lines 113-6B, 113-10B, 113-30B, and 113-31B the expression of tumor suppressor gene p27 was confirmed by immunofluorescence and the production of SEAP was monitored by the classical enzymatic test for alkaline phosphatases. Conditional expression of Bcl-x$_L$ was addressed by Western blot analysis as described above.

The proliferation potential as well as the productivity of the three cell lines DD6-X1, DD6-X2, and DD6-X3 was subsequently determined as described above using the same control cell line 111-10. These cell lines, when shifted to tetracycline-free medium which activates the expression of all genes encoded in the tricistronic expression unit, are proliferation-arrested to different degrees with DD6-X1 and DD6-X2 showing an almost complete growth inhibition while the growth arrest of DD6-X3 is more relaxed. As their dicistronic counterparts transfected with pMF113, the tricistronic cell lines DD6-X1, DD6-X2 DD6-X3 did not show any morphological signs of apoptosis under cytostatic conditions. However, with the bcl-x$_L$ gene included, the per cell SEAP activity of DD-X1 and DD-X2 increased by an additional factor of 3 compared to their dicistronic counterparts (see above), reaching values of 30 times greater than the per cell productivity observed with the proliferating control cell line (111-10). The exact role of the anti-apoptotic gene bcl-x$_L$ in this observed increase in per cell productivity remains to be elucidated. The cell line DD-X3 which displays a less restrained growth behavior in tetracycline-free medium displays also a much lower overall SEAP productivity. Such a direct correlation between the extent of the growth arrest and the amount of model product protein produced was also observed for the respective cell lines 113-10B and 113-30B engineered with the isogenic, dicistronic expression vector.

10.2.2 Co-ordinated Expression of p21 and the Differentiation Factor C/EBPα Results in Higher Productivity and Growth Inhibition Because attempts to use the tumor suppressor gene p21 for controlled proliferation in stably transfected CHO cells were unsuccessful, we constructed a tricistronic expression vector, pSS5, which is isogenic to pDD1 and pDD3 but contains the differentiation factor c/ebpα in the third cistron instead of the survival factors bcl-2 and bcl-x$_L$, respectively (FIG. 5). C/EBPα influences terminal differentiation by inducing p21 and maintains the differentiated state of certain cells by stabilizing p21 at the protein level. One reason for the failure to get stable clones which arrest upon induction of p21 using pMF112 or pDD1 could be related to the relative high intracellular concentration needed to exhibit proliferation inhibition. As the intracellular p21 concentration is limited by the expression level and the breakdown of this cdi, we expected to increase intracellular p21 concentration by the overexpression of c/ebpα which stabilizes p21 at the protein level. Indeed, when we transfected pSS5 into XMK1–9, four stable clones SS5-127, SS5-135, SS5-153, and SS5-156 were generated. Upon induction of the tricistronic expression unit these cells show correlated overexpression of p21 and C/EBPα in immunofluorescence analysis. As shown above for the other cell lines engineered for controlled proliferation, these cell lines differ in the extent of growth arrest upon induction of the tricistronic expression unit. Whereas cell lines SS5-153, SS5-127, and SS5-156 show a sustained growth arrest over the five days tested, the cell line SS5-135 almost equals the control cell line in its growth behavior (see FIG. 8).

As described above for cell lines stably transfected with pMF113 and pDD6, the SEAP productivity of such cell lines is dependent on and correlates with their potential to remain inert to proliferative signals. Specifically, cell lines SS5-153, SS5-127, and SS5-156 show a roughly 10 (SS5-127, SS5-156) to 15 (SS5-153) times higher overall SEAP productivity than the proliferation competent control cell line 111-10 whereas the SEAP productivity of SS5-135 shows almost no increase (see FIG. 7). As for the proliferation-controlled cell lines described above, growth-arrested cell lines harboring the SS5 derivative show no other changes in their morphology but a slight increase in their overall surface.

10.3 Discussion

Using the tricistronic expression technology described above in Section 9, we combined controlled proliferation technology with anti-apoptosis engineering by expressing, in addition to SEAP and p27, either bcl-2 or the closely related bcl-x$_L$. Cells harboring SEAP-p27-bcl-x$_L$ are, when shifted to a medium which activates expression of theses genes, proliferation arrested. They do not show any sign of apoptosis (nor do the cells in the prior examples without the anti-apoptosis gene added). However, with the bCl-x$_L$ gene included, the per cell activity of SEAP now increases by an additional factor of 3, reaching values of 30 times greater than the per cell productivity observed with unmodified proliferating cells.

An increase in productivity following overexpression of the survival gene bcl-2 has already been observed for hybridoma cells (Itoh et al., 1995, supra). The overexpression of bcl-x$_L$ has recently been shown to lead to polyploidy (Minn et al., 1996, Genes and Dev. 10:2621–2631). An increase in genetic information could thus explain the corresponding additional increase in SEAP productivity of proliferation-inhibited cells.

Since intracellular p21 levels are limited by expression and turnover of p21, we increased nuclear p21 concentrations by expression of the p21-stabilizing and inducing factor C/EBPα using the tricistronic expression technology described above. CHO cells stably transfected with SEAP-p21-c/ebpα containing constructs show the same sustained growth arrest and increase in productivity on a per cell basis as the SEAP-p27 containing cells (up to 15-fold increase). Both cell lines resume growth upon repression of the tumor suppressor gene even following prolonged periods of growth inhibition indicating that proliferation-inhibition does not reduce cell viability or induce programmed cell death.

11. EXAMPLE

Autoregulation Via a Transactivator in a Multicistronic Vector

11.1 Materials and Methods

CHO cell culture, transfection, immunofluorescence and flow cytometry were performed as described above. Baby hamster kidney cells (BHK-21, ATCC: CRL-8544) and HeLa (ATCC: CRL-7923) were also cultured in FMX-8 medium (Dr. F. Messi Cell Culture Systems, Switzerland) supplemented with 10% fetal calf serum (FCS, Boehringer Mannheim).

11.1.1 Plasmid Constructions

The tetracycline-regulatable transactivator (tTA) contained in pUHD15-1 (Gossen and Bujard, 1992, supra) was restricted by EcoRI/BamHI and ligated to the corresponding restriction sites of pSBC-2 (Dirks et al., 1993, supra) to give pSAM200. The IRES-tTA-pA-ori-bla-containing SspI/NotI fragment was subsequently fused to the SspI/NotI fragment of pMF102 (described above) harboring the tetracycline-regulatable promoter PhCMV*-1 as well as the humanized green fluorescent protein, hGFP-S65T (GFP-S65T, Clonetech laboratories, Palo Alto; Heim et al., 1995, supra). This plasmid (pSAM202) contains GFP and tTA as a dicistronic expression unit under the control of a single PhCMV*-1 promoter. The translation of the second cistron (tTA) is mediated by the pircornaviral internal ribosomal entry site (IRES).

In order to construct a tricistronic expression vector containing tTA in one of the three cistrons, we amplified tTA of pUHD15-1 with oligos OSM1: GATCACTAGTGCGGCCGCGAATTCATAT-GTCTAGAT (SEQ ID NO:19) and

OSM2: GATCACGCGTATCGATAAGCTTCTAC-CCACCGTACTCGTC (SEQ ID NO:20).

The PCR product was ligated blunt-ended into the pCR-Script Amp SK(+) (Stratagene) to give pSAM201. The tTA gene was subsequently restricted with EcoRI/HindIII contained in extensions of the oligos and ligated into the first multiple cloning site of pTRIDENT1 (described above) via corresponding sites to give pTRIDENT-tTA. To provide evidence for simultaneous as well as adjustable expression of two additional genes (besides tTA in the first cistron), the cytostatic tumor suppressor gene p21 and GFP cycle 3 mutant (Affimax Research Institute, Palo Alto, Crameri et al., 1996, supra) were cloned into cistron two and three, respectively. This expression vector, pSAM204, containing the tricistronic expression unit (tTA-p21-GFP) under the control of P$_{hCMV*-1}$ was cloned by fusing pTRIDENT-tTA and pMF132 (described above) via their NotI/SspI restriction sites.

pQuattro-tTA, the quattrocistronic expression vector is isogenic to pTRIDENT-tTA but harbors an additional genetic element for cap-independent translation enhancement from the encephalomyocarditis virus (IRES-EV) followed by the neomycin resistance gene (neo). pQuattro-tTA was constructed by fusing pTRIDENT-tTA and pIRES1neo (Clonetech) via their BglII/SspI restriction sites.

11.2 Results 11.2.1 Simultaneous and Co-ordinated Expression of tTA and GFP in CHO Cells The dicistronic expression vector pSAM202 (FIG. 9) unites the green fluorescent protein (GFP, hGFP-S65T) and the tetracycline-regulated transactivator tTA in a single "artificial operon" under the control of the tTA responsive promoter PhCMV*-1. pSAM202 was transiently transfected into wild type CHO-K1 cells. The first few dicistronic transcripts which arise due to the leakiness of PhCMV*-1 allow the cap-independent translation of tTA encoded on the second cistron. Such initial production of tTA subsequently, in the absence of tetracycline, transactivates and induces PhCMV*-1. This genetic configuration generates a positive feedback circuit leading to a high steady-state intracellular concentration of the transactivator and concomitantly high PhCMV*-1 activity. CHO-K1 cells expressing GFP from transiently transfected pSAM202 show bright green fluorescence which, as judged by microscopical examination is at least as high as the fluorescence intensity observed upon transfection of XMK1-9, a CHO derivative constitutively expressing tTA, with the isogenic control plasmid pMF102. Despite a presumably high intracellular tTA concentration resulting from the positive feedback circuit, GFP expression from pSAM202 remains adjustable in response to tetracycline at any time point following transfection and can be reversibly switched on and off. Consequently, in the presence of exogenous tetracycline the intrinsic basal activity of the PhCMV*-1 promoter does not result in detectable amounts of GFP. Judged from fluorescence microscopic examination, repression of GFP expression is much tighter using CHO-K1 and pSAM202 as compared to GFP repression by tetracycline in XMK1–9 and pMF102 in which tTA is expressed constitutively (data not shown).

11.2.2 Positive Feedback Regulation of GFP and p21 in CHO-KL Using a Tricistronic Expression Vector As the obligatory presence of tTA in the dicistronic expression unit limits the capacity of the positive feedback regulation system to transcriptional control of expression of a single additional cloned gene, we extended this system by adding a further cap-independent translation unit in order to allow the tetracycline-regulatable expression of two heterologous proteins. Based on the results above which show that a tricistronic expression unit containing two identical IRES elements remains stable in CHO cells and leads to the expression of three different proteins (see Section 10), we constructed pSAM204 (FIG. 9). In contrast to pSAM202 where tTA translation is IRES-mediated, its expression from pSAM204 is cap-dependent as tTA is encoded by the first cistron. Both of the next cistrons, the cytostatic gene p21 and GFP are preceded by an identical IRES element. Together with tTA, these form the tricistronic expression unit contained on pSAM204.

Transient transfection of pSAM204 into CHO-K1 leads to simultaneous as well as tetracycline-adjustable regulation of p21 and GFP. The expression of p21 and GFP was strictly correlated and reaches expression levels, as monitored by immunofluorescence microscopy, which are identical to pMF132 harbouring p21 and GFP in the second and third cistron, respectively, or to the GFP expression of pSAM202. The comparison of pSAM202 and pSAM204 with respect to GFP expression indicates that positive feedback regulation is functional and equally efficient independent of whether tTA is translated in a cap-dependent (pSAM204) or IRES-mediated manner (pSAM202).

11.2.3 Positive Feedback Regulation Vectors are Functional in HeLa and BHK Cells Since the positive feedback regulation plasmids pSAM202 and pSAM204 combine all genetic elements necessary to express up to two heterologous proteins in an adjustable and co-ordinated manner in a single expression vector, we tested its self-sufficient potential in two additional biotechnologically relevant cell lines. When pSAM202 and pSAM204 were transfected into HeLa and BHK-21 cells using the identical transfection protocol as used for the CHO cells, transfected cells of both cell types emitted strong green light when examined under the fluorescence microscope 48 hours after transfection. The GFP expression could be reversibly switched on and off following withdrawal or addition of tetracycline in the culture medium, respectively. The expression of GFP by the positive feedback regulation system showed no detrimental effect and the cell morphology remained unchanged when compared to HeLa and BHK-21 cells transfected with phGFP-S65T or Alpha+GFP, control plasmids that harbor the isogenic GFPs under the control of the constitutive viral promoter (Cheng et al., 1996, supra; Crameri et al., 1996, supra; Levy et al., 1996, supra). However, as already observed for CHO cells, HeLa and BHK-21 cells show a significant increase in their cell volume when detached from the surface. This might indicate a high production of GFP which accumulates in the cell although immunofluorescence data are not indicating a higher fluorescence intensity. Such phenomena have already been observed and were attributed to intracellular aggregation of GFP into fluorescence incompetent complexes (Crameri et al., 1996, supra).

11.2.4 Multicistronic Expression Vectors Harboring the Positive Feedback Regulation System As multicistronic expression vectors harboring the positive feedback regulation mechanism were shown to function in three different cell lines we expect this system to have the potential to work in a wide variety of other cell types. Two additional, general purpose expression vectors, pTRIDENT-tTA and pQuattro-tTA, both containing PhCMV*-1 and tTA which are required for positive feedback regulation, were constructed (FIG. 9). pTRIDENT-tTA contains tTA in the first cistron as in pSAM204, followed by two consecutive, identical picornaviral IRES elements (IRESI and IRESII) which promote cap-independent translation of cistrons II and cistron III. Genes of these two cistrons can be integrated into two different multiple cloning sites containing a total of 15 unique restriction sites including 8 eight base pair cutters.

pQuattro-tTA is identical to pTRIDENT-tTA but contains the neomycin resistance marker (neo) as its fourth cistron, the translation of which is mediated by a further cap-independent translation enhancer (IRES-EV) from the encephalomyocarditis virus (ECMV). The IRES-EV element harbors a mutation (IRES-EV) which considerably lowers the translation efficiency of this element (Rees et al., 1996, supra). The lower translation efficiency of the neomycin resistance gene is expected to be compensated in stable clones by the selection for genome integration sites with high gene expression, or by amplification of the integrated vector, in order to survive high concentrations of G418. The presence of an antibiotic resistance marker in the last cistron of a multicistronic expression vector guarantees the expression of upstream cistrons in almost all selected stable clones.

11.3 Discussion

The tetracycline-controlled inducible system for gene expression in higher eukaryotes by Gossen and Bujard (1992), et al., consists of two components, the transcription factor tTA and the inducible promoter responsive to tTA-mediated activation. Stable expression of even moderate levels of tTA in some mammalian cells proves to be difficult and has been attributed to the squelching effect of the VP16 domain (Gill and Ptashne, 1988, supra; Ptashne and Gann, 1990, Nature 346,329–331; Trienzenberg et al., 1988, Genes Dev. 2, 718–719). Consequently, it is difficult to clone cells stably transfected with tTA which produce non-toxic levels of tTA which also show highly active expression of the heterologous protein upon induction (Gossen and Bujard, 1992, supra). Yoshida and Hamada (1997), supra, alleviated this problem by adding the nuclear localization signal sequence to the carboxy-terminus of the transactivator which targets tTA with higher efficiency to the cell nucleus without the need for an overall higher tTA expression. In a contrasting attempt, Iida et al., (1996), supra, negatively regulated the transfer of tTA to the cell nucleus by adding the ER ligand-binding domain to the carboxy-terminus of the tTA (tTAER) which reduces tTA uptake by the nucleus in the absence of estradiol or derivatives and consequently lowers tTA toxicity even if constitutively expressed.

An alternative approach, which also aims at reducing tTA toxicity, places the tTA under the control of its own target promoter, PhCMV*-1 (Shocket et al., 1995, Proc. Natl. Acad. Sci. USA 92, 6522–6526). However, this approach, as previously implemented, requires separate cloning, in two successive steps, of the autoregulated tTA gene and the product gene of interest. Besides the significantly greater time required, screening is then needed to identify clones with suitable transcription regulation properties. Although there are plasmids available which combine tTA and the gene of interest as two independent cistrons (Paulus et al., 1996, J. Virol 70, 62–67; Schultze et al., 1996, Nat. Biotechnol. 14, 499–503), these vectors provide constitutive tTA expression with the same toxicity problems as discussed above.

In this experiment we combined tTA as well as the product gene(s) of interest not only on a single plasmid but in a single mRNA transcript using our multicistronic expression technology. As the single mRNA transcript is driven by PhCMV*-1, the presence of tTA in such a multicistronic expression unit guarantees both (i) little or no tTA, and product, expression in the presence of tetracycline and (ii) high induction and positive feedback activation of product expression upon withdrawal of tetracycline from the culture medium. The multicistronic expression technology described here allows up to two additional genes of interest to be coexpressed in a co-ordinated and regulatable fashion which makes this adapted system especially useful for multi-gene engineering of mammalian cells with two-component factors or antibodies. Since the function of the positive feedback regulation functions independent of cap-dependent or cap-independent translation, multicistronic, positive feedback regulation systems such as pSAM202 are autoselective in stably transfected cells. Further, the observed expression of the system guarantees that all cistrons upstream of tTA remain intact. Similar selective pressure is present in pQuattro-tTA where the fourth cistron contains the antibiotic resistance gene. Additionally, the cap-independent translation enhancer was mutated to lower the expression of the neomycin resistance gene which should direct the transcript at highly expressed places of the genome to compensate for the engineered translational downregulation of antibiotic resistance. By combining multiple features in a single expression vector our positive feedback regulation vectors harbor the most versatile tet system implementing all properties for optimal use in a wide variety of mammalian cells.

EQUIVALENTS

The foregoing written specification is sufficient to enable one skilled in the art to practice the invention. Indeed, various modifications of the above-described means for carrying out the invention which are obvious to those skilled in the field of molecular biology, cell biology or related fields are intended to be within the scope of the following claims.

What is claimed is:

1. A method for production of a desired product from a cell, the method comprising:
culturing a cell that has been genetically engineered to inducibly express a tumor suppressor gene product under conditions such that expression of the tumor suppressor gene product is induced, thereby arresting cell proliferation; and
collecting the desired from the cultured cell.

2. The method of claim 1, wherein the tumor suppressor gene product is selected from the group consisting of p21, p27, p53, p53175P, p57, p15, p16, p18, p19, p73, GADD45, APC1 and p73.

3. The method of claim 1, wherein an inducible promoter is operably linked to a first polynucleotide sequence encoding the tumor suppressor gene product.

4. The method of claim 1, wherein prior to said culturing step, the cell is transfected with an expression vector that encodes the tumor suppressor gene product.

5. The method of claim 1, wherein prior to said culturing step, the cell is cultured under proliferating conditions.

6. The method of claim 1, wherein the cultured cell is a mammalian cell.

7. The method of claim 1, wherein the product is coordinately expressed with the tumor suppressor gene product.

8. The method of claim 3, wherein the inducible promoter is selected from the group consisting of a tetracycline-responsive promoter, an ecdysone-inducible promoter, a metallothionein-regulated promoter, a steroid-regulated promoter, and a heat-shock regulated promoter.

9. A method for production of a desired product from a cell, the method comprising:
culturing a cell under conditions such that expression of a tumor suppressor gene product is induced, thereby arresting cell proliferation;
expressing an antiapoptosis gene product in the cultured cell; and
collecting the desired from the cultured cell.

10. The method of claim 9, wherein the antiapoptosis gene product is selected from the group consisting of bcl-2, bcl-$x_L$, E1B-19K, mcl-1, crmA, abl, p35, bag-1, A20, LMP-1, Tax, Ras, Rel and NF-κB.

11. The method of claim 9, wherein the antiapoptosis gene product is coordinately expressed with the tumor suppressor gene product.

12. A method for production of a desired product from a cell, the method comprising:
culturing a cell under conditions such that expression of a tumor suppressor gene product is induced, thereby arresting cell proliferation;
expressing a factor that stabilizes the tumor suppressor gene product in the cultured cell; and
collecting the desired from the cultured cell.

13. The method of claim 12, wherein the factor that stabilizes the tumor suppressor gene product is c/ebpα.

14. The method of claim 12, wherein the factor that stabilizes the tumor suppressor gene product is coordinately expressed with the tumor suppressor gene product.

15. The method of claim 11, wherein the product, the tumor suppressor gene product and the antiapoptosis gene product are encoded on the same RNA.

16. The method of claim 14, wherein the product, the tumor suppressor gene product and the factor that stabilizes the tumor suppressor gene product are encoded on the same RNA.

17. A method for production of a desired product from a cell, the method comprising:
culturing a cell under conditions such that expression of a tumor suppressor gene product is induced, thereby arresting cell proliferation;
expressing the product coordinately with the tumor suppressor gene product, wherein the product is selected from the group consisting of green fluorescent protein, SEAP, human growth hormone, α-interferon, β-interferon, γ-INF, insulin, erythropoietin, tissue plasminogen activator, DNAse, a monoclonal antibody, Factor VIII, Factor VII, Factor IX, HSA, IL-2, glucagon, EGF, GCSF, GMCSF, thrombopoietin, gp160 and HbSAg; and
collecting the desired from the cultured cell.

18. A method for production of a desired product from a cell, the method comprising:
culturing a cell under conditions such that expression of a tumor suppressor gene product is induced, thereby arresting cell proliferation;
expressing the product coordinately with the tumor suppressor gene product, wherein the product and the tumor suppressor gene product are encoded on the same RNA; and
collecting the desired from the cultured cell.

19. A mammalian cell that has been genetically engineered to inducibly a desired product gene and a tumor suppressor gene.

20. The mammalian cell of claim 19 wherein the tumor suppressor gene is selected from the group consisting of p21, p27, p53, p53175P, p57, p15, p16, p18, p19, p73, GADD45, APC1 and p73.

21. A mammalian cell that has been genetically engineered to express an antiapoptosis gene and to inducibly express a tumor suppressor gene.

22. The mammalian cell of claim 21 wherein the tumor suppressor gene is selected from the group consisting of p53, p21 and p27, and the antiapoptosis gene is selected from the group consisting of bcl-2 and bcl-$x_L$.

23. A mammalian cell that has been genetically engineered to inducibly express a tumor suppressor gene and to express a factor that stabilizes the tumor suppressor gene product in the cell.

24. The mammalian cell of claim 23 wherein the tumor suppressor gene is p21 and the factor that stabilizes the tumor suppressor gene product is c/ebpα.

25. A recombinant polynucleotide vector comprising:
a first nucleic acid sequence encoding a product protein; and
a second nucleic acid sequence encoding a tumor suppressor gene product, wherein the first nucleic acid sequence is operatively linked to a first inducible promoter and the second nucleic acid sequence is operatively linked to either the first inducible promoter or to a second inducible promoter.

26. The vector of claim 25, wherein the sequence encoding the product protein and the sequence encoding the tumor suppressor gene product are cocistronically expressed.

27. The vector of claim 25, wherein the tumor suppressor gene product is selected from the group consisting of p21, p27, p53, p53175P, p57, p15, p16, p18, p19, p73, GADD45, APC1 and p73.

28. The vector of claim 25, wherein the inducible promoter is selected from the group consisting of a tetracycline-responsive promoter, an ecdysone-inducible promoter, a metallothionein-regulated promoter, a steroid-regulated promoter, and a heat-shock regulated promoter.

29. A host cell that contains the vector of claim 25.

30. The vector of claim 26, wherein translation of the sequence encoding the product protein or the sequence encoding the tumor suppressor gene product is controlled by an internal ribosomal entry site.

31. The vector of claim 30, wherein the internal ribosomal entry site is a picornaviral IRES element.

32. A recombinant polynucleotide vector comprising:
a sequence encoding a product protein;
a sequence encoding a tumor suppressor gene product; and
an inducible promoter operatively linked to the sequence encoding a tumor suppressor gene product, wherein the vector further comprises a sequence encoding an antiapoptosis gene product or a factor that stabilizes the tumor suppressor gene product in the cell.

33. The vector of claim 32, wherein the antiapoptosis gene product is selected from the group consisting of bcl-2, bcl-$x_L$, E1B-19K, mcl-1, crmA, abl, p35, bag-1, A20, LMP-1, Tax, Ras, Rel and NF-κB.

34. The vector of claim 32, wherein the factor that stabilizes the tumor suppressor gene product is c/ebpα.

35. The vector of claim 32, wherein the third sequence is cocistronic with the sequence encoding the product protein and the sequence encoding the tumor suppressor gene product.

36. The host cell of claim 29, wherein the cell is stably transformed by the vector.

37. A host cell that contains a recombinant polynucleotide vector, wherein the host cell is selected from the group consisting of an insect cell, a fungal cell, a reptilian cell, a CHO cell, a BHK cell, a HeLa cell, a PLC cell, a Jurkat cell, a HT-1080 cell, a Hep2 cell, an ECV304 cell, a COS-7 cell, a NIH/3T3 cell, a HaCat cell, a LCL cell, a HUVEC cell, a NSO cell and a HL60 cell; and wherein the host cell is stably transformed by a vector comprising:

a sequence encoding a product protein;

a sequence encoding a tumor suppressor gene product; and an inducible promoter operatively linked to the sequence encoding the product protein and the tumor suppressor gene product.

* * * * *

```
                          SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (xi) SEQUENCE DESCRIPTION: SEQ ID NO:1:

GATCGAATTC GACCGGAAGC TTGCCGCC                                           28

(2) INFORMATION FOR SEQ ID NO:2:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (xi) SEQUENCE DESCRIPTION: SEQ ID NO:2:

GATCGTCGAC TTACTTGTAC AGCTCGTCC                                          29

(2) INFORMATION FOR SEQ ID NO:3:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (xi) SEQUENCE DESCRIPTION: SEQ ID NO:3:

GATCGAATTC TTCGCCGAGG CACCGAGG                                           28

(2) INFORMATION FOR SEQ ID NO:4:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (xi) SEQUENCE DESCRIPTION: SEQ ID NO:4:

GATCAAGCTT TTAGGGCTTC CTCTTGGAG                                          29
```

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:5:

GATCGAATTC GCGGTCGTGC AGACCCGG                      28

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:6:

GATCAAGCTT TTACGTTTGA CGTCTTCTG                     29

(2) INFORMATION FOR SEQ ID NO:7:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (xi) SEQUENCE DESCRIPTION: SEQ ID NO:7:

GATCGAATTC GCGGCCGCGG CCGGCCCGGG CGCGCCTGAT CAATCGATGT TTAAACTTAA    60

AACAGCTCTG GGGT                                                 74

(2) INFORMATION FOR SEQ ID NO:8:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:8:

GATCAGATCT GTTTAAACGC GTATTTAAAT TAATTAAGCG ATCGCACTAG TCTCGAGAAT    60

CCAATTCGCT TTATG                                               75

(2) INFORMATION FOR SEQ ID NO:9:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:9:

GATCGAATTC GCGGCCGCGG CCGGCCCGGG CGCGCCTGAT CAATCGATGT TTAAACGTTA    60

TTTTCCACCA TATTG                                               75

(2) INFORMATION FOR SEQ ID NO:10:

(i) SEQUENCE CHARACTERISTICS:
        (A) LENGTH: 75 base pairs
        (B) TYPE: nucleic acid

```
         (C) STRANDEDNESS: single
         (D) TOPOLOGY: linear (xi) SEQUENCE DESCRIPTION: SEQ ID NO:10:

GATCAGATCT GTTTAAACGC GTATTTAAAT TAATTAAGCG ATCGCACTAG TCTCGAGAAT        60

CGTGTTTTTC AAAGG                                                        75

(2) INFORMATION FOR SEQ ID NO:11:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (xi) SEQUENCE DESCRIPTION: SEQ ID NO:11:

GATCACTAGT GATATCGCGG CCGCTTCGCC GAGGCACCGA GG                           42

(2) INFORMATION FOR SEQ ID NO:12:

(i) SEQUENCE CHARACTERISTICS:
         (A) LENGTH: 43 base pairs
         (B) TYPE: nucleic acid
         (C) STRANDEDNESS: single
         (D) TOPOLOGY: linear (xi) SEQUENCE DESCRIPTION: SEQ ID NO:12:

GATCATCGAT GGATCCGCCC GGGCTTAGGG CTTCCTCTTG GAG                          43

(2) INFORMATION FOR SEQ ID NO:13:

(i) SEQUENCE CHARACTERISTICS:
         (A) LENGTH: 44 base pairs
         (B) TYPE: nucleic acid
         (C) STRANDEDNESS: single
         (D) TOPOLOGY: linear (xi) SEQUENCE DESCRIPTION: SEQ ID NO:13:

GATCACTAGT GCGATCGCTT AATTAAGATC CAAGCTGCCT CGAG                         44

(2) INFORMATION FOR SEQ ID NO:14:

(i) SEQUENCE CHARACTERISTICS:
         (A) LENGTH: 43 base pairs
         (B) TYPE: nucleic acid
         (C) STRANDEDNESS: single
         (D) TOPOLOGY: linear (xi) SEQUENCE DESCRIPTION: SEQ ID NO:14:

GATCAGATCT ACGCGTATTT AAATTTACTT GTACAGCTCG TCC                          43

(2) INFORMATION FOR SEQ ID NO:15:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (xi) SEQUENCE DESCRIPTION: SEQ ID NO:15:

GATCGAATTC GATCCAAGCT TGCCTCGAG                                          29
```

(2) INFORMATION FOR SEQ ID NO:16:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:16:

```
GATCCTGCAG CCCGGGTTAT TTGTAGAGCT CATC                                34
```

(2) INFORMATION FOR SEQ ID NO:17:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:17:

```
GATCACTAGT GATATCGCGG CCGCGCGGTC GTGCAGACCC GG                       42
```

(2) INFORMATION FOR SEQ ID NO:18:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:18:

```
GATCATCGAT GGATCCGCCC GGGCTTACGT TTGACGTCTT CTTCTG                   46
```

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:19:

```
GATCACTAGT GCGGCCGCGA ATTCATATGT CTAGAT                              36
```

(2) INFORMATION FOR SEQ ID NO:20:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:20:

```
GATCACGCGT ATCGATAAGC TTCTACCCAC CGTACTCGTC                          40
```